(12) United States Patent
Rao et al.

(10) Patent No.: US 9,677,112 B2
(45) Date of Patent: *Jun. 13, 2017

(54) β-LACTAMASE SUBSTRATES AND METHODS OF THEIR USE FOR THE DIAGNOSIS OF TUBERCULOSIS

(71) Applicants: The Texas A&M University System, College Station, TX (US); The Board of Trustees of the Leland Stanford Junior University, Palo Alto, CA (US)

(72) Inventors: Jianghong Rao, Sunnyvale, CA (US); Jeffrey D. Cirillo, College Station, TX (US); Hexin Xie, Mountain View, CA (US); James C. Sacchettini, College Station, TX (US)

(73) Assignees: The Texas A&M University System, College Station, TX (US); The Board of Trustees of the Leland Stanford Junior University, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/401,775

(22) PCT Filed: May 15, 2013

(86) PCT No.: PCT/US2013/041244
§ 371 (c)(1),
(2) Date: Nov. 17, 2014

(87) PCT Pub. No.: WO2013/173519
PCT Pub. Date: Nov. 21, 2013

(65) Prior Publication Data
US 2015/0167048 A1    Jun. 18, 2015

Related U.S. Application Data

(60) Provisional application No. 61/647,374, filed on May 15, 2012.

(51) Int. Cl.
*C07D 501/34* (2006.01)
*C12Q 1/34* (2006.01)
*C07D 501/24* (2006.01)
*C07D 501/26* (2006.01)
*C07D 501/30* (2006.01)
*C07D 501/57* (2006.01)

(52) U.S. Cl.
CPC ............. *C12Q 1/34* (2013.01); *C07D 501/24* (2013.01); *C07D 501/26* (2013.01); *C07D 501/30* (2013.01); *C07D 501/34* (2013.01); *C07D 501/57* (2013.01); *G01N 2333/986* (2013.01); *G01N 2800/26* (2013.01)

(58) Field of Classification Search
None
See application file for complete search history.

(56) References Cited

U.S. PATENT DOCUMENTS

| 2007/0020715 A1 | 1/2007 | Tsien |
| 2008/0014602 A1* | 1/2008 | Nagano ................... C09B 11/08 435/18 |
| 2011/0020240 A1* | 1/2011 | Cirillo et al. ................. 424/9.6 |

FOREIGN PATENT DOCUMENTS

| WO | 2005/071096 A2 | 8/2005 |
| WO | 2011/152883 A2 | 12/2011 |

OTHER PUBLICATIONS

International Search Report and Written Opinion mailed Sep. 27, 2013, issued in corresponding International Application No. PCT/US2013/041244, filed May 15, 2013, 12 pages.
Xie, H., et al., "Rapid Point-of-Care Detection of the Tuberculosis Pathogen Using a BlaC-Specific Fluorogenic Probe," Nature Chemistry 4(10):802-809, Oct. 2012.

* cited by examiner

*Primary Examiner* — Golam M M Shameem
*Assistant Examiner* — Laura Daniel
(74) *Attorney, Agent, or Firm* — Christensen O'Connor Johnson Kindness PLLC

(57) ABSTRACT

β-Lactamase substrates and methods for using the substrates to detect β-lactamase diagnose tuberculosis.

22 Claims, 24 Drawing Sheets

Houston Samples
Smear+/Culture+/REF+

Smear-/Culture+/REF+

Smear-/Culture-/REF-

Peru Samples
Smear+/GeneXpert+/REF+

Smear-/GeneXpert+/REF+

Smear-/GeneXpert-/REF-

β-LACTAMASE SUBSTRATES AND METHODS OF THEIR USE FOR THE DIAGNOSIS OF TUBERCULOSIS

CROSS REFERENCES TO RELATED APPLICATIONS

This application is the National Stage of International Application No. PCT/US2013/41244, filed May 15, 2013, which claims the benefit of U.S. Patent Application No. 61/647,374, filed May 15, 2012; each disclosure is expressly incorporated herein by reference in its entirety.

BACKGROUND OF THE INVENTION

*Mycobacterium tuberculosis* (Mtb) is a widespread pathogenic bacterial species that causes tuberculosis, one of the most deadly diseases, killing over one million people each year and infecting one third of the world's population. Early diagnosis is critical to the prevention and control of tuberculosis due to its airborne transmission. Standard diagnostic methods, acid-fast smear from sputum, do not become positive until after transmission can occur, allowing spread of disease. Culture-based techniques are more sensitive, but take weeks to obtain results, due to the extremely slow growth rate of Mtb. Tuberculosis research and clinical diagnosis would be greatly facilitated by methods that can detect tubercle bacilli in a sensitive, rapid, specific and quantitative manner in vitro and during disease.

Tubercle bacilli naturally express beta-lactamase (BlaC), an enzyme that belongs to the class A β-lactamase family. Extended spectrum class A β-lactamases are capable of hydrolyzing all classes of β-lactam substrates, including cephalosporins. The mechanism of cephalosporin hydrolysis by β-lactamases yields hydrolyzed β-lactam, and more importantly, may be concomitant with the loss of the 3' leaving group, depending on the group. Based on this mechanism, a number of fluorogenic and bioluminogenic probes have been developed for detection of β-lactamase activity in vitro, in living cells, and even in whole animals.

Current probes lack specificity for BlaC in Mtb; the common TEM-1 β-lactamase (TEM-1 Bla) in gram-negative bacteria can also generate fluorescence with these probes, which would reduce their accuracy for use in tuberculosis diagnosis. These probes are generally large and display slow hydrolytic kinetics for BlaC.

Despite the advances in the development of fluorescent probes for the detection of beta-lactamase and the diagnosis of tuberculosis, a need exists for novel probes that facilitate the rapid detection of tuberculosis. The present invention seeks to fulfill this need and provides further related advantages.

SUMMARY OF THE INVENTION

The present invention provides β-lactamase substrates and methods for using the substrates to detect β-lactamase and to diagnose tuberculosis.

In one aspect, the invention provides a β-lactamase substrates.

In one embodiment, the invention provides a compound having Formula (I):

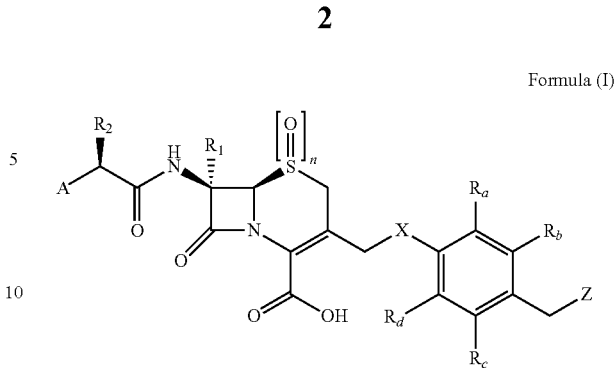

Formula (I)

or an ester or a salt thereof.

In another embodiment, the invention provides a compound having Formula (II):

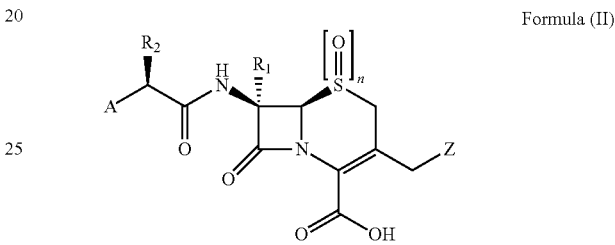

Formula (II)

or an ester or a salt thereof.

In a further embodiment, the invention provides a compound having Formula (III):

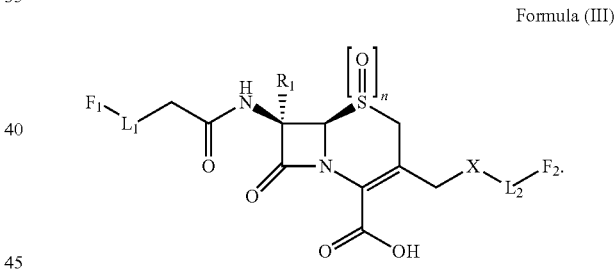

Formula (III)

or an ester or a salt thereof.

In another aspect of the invention, methods for detecting β-lactamase are provided.

In a further aspect of the invention, methods for diagnosing tuberculosis are provided.

DESCRIPTION OF THE DRAWINGS

The foregoing aspects and many of the attendant advantages of this invention will become more readily appreciated as the same become better understood by reference to the following detailed description.

FIG. 1A compares the fluorescent emission spectrum of CDC-OMe (1 μM in PBS) before and after treatment with BlaC (1 μM) (excitation: 400 nm). FIGS. 1B and 1C compare time courses of fluorescent activation of probes with BlaC (FIG. 1B) and TEM-1 Bla (FIG. 1C). FIGS. 1D and 1E compare enhanced fluorescent intensity of CDC-OMe (FIG. 1D) and CDC-1 (FIG. 1E) (5 μM in PBS) by serially diluted solutions of BlaC or TEM-1 Bla for 1 hour. $F/F_0$ represents the turn-on ratio by β-lactamase (F: fluorescent intensity of probe incubated with β-lactamase, $F_0$: fluorescent intensity of the probe incubated in buffer; a.u.: absorbance units).

FIG. 2A illustrates conserved salt bridges in both enzymes formed by D172-R178 and D176-R178 stabilize the loop conformers of the unoccupied active sites. FIG. 2B illustrates TEM-1 Bla R164 forms salt bridges with D171 (2.87 Å), D176 (3.99 Å), and D179 (2.75 Å). BlaC A164 prevents these stabilizing interactions, and increases flexibility of catalytic base E166.

FIG. 3A illustrates electrostatic surface potential and FIG. 3b illustrates cartoon diagrams of acyl-intermediates with $F_O$-$F_C$ electron density maps displayed in green for CDC-OMe (2.0σ) and CDC-1 (1.5σ) prior to fitting each ligand for refinement protocols. FIG. 3C illustrates active site residues displayed as sticks and Ligplot analysis of active site interactions.

FIG. 4A illustrates a superimposition of unoccupied TEM-1 Bla and BlaC active sites. FIG. 4B illustrates a superimposition of unoccupied TEM-1 Bla and BlaC-CDC-OMe acyl-intermediate complex.

FIG. 5A is a schematic illustration of BlaC hydrolysis of the substrates that turns on fluorescence signal. FIG. 5B compares the fluorescent emission spectra of CDG-OMe (20 nM in MES) before and after treatment of BlaC (0.2 µM) (excitation: 490 nm). FIG. 5C compares the time course of fluorescence enhancement with CDG-OMe (8 µM in MES) and various concentrations of β-lactamases. FIG. 5D compares enhanced fluorescence intensity of CDG-OMe (8 µM in MES, front) and CDG-1 (8 µM in MES, back) by serially diluted solutions of BlaC or TEM-1 Bla for 8 hours. ΔF represents the difference of fluorescence intensity between incubating with and without β-lactamases. Data were collected in 384-well plates with a total volume of 25 mL in each well. FIG. 5E is a magnified view of the low concentration region in FIG. 5D. Data in FIGS. 5D and 5E are the average of three replicate experiments.

FIG. 6A compares detection of TEM-1 Bla- and BlaC-expressing E. coli with CDG-1. FIG. 6B compares detection of TEM-1 Bla- and BlaC-expressing E. coli with CDG-OMe. For FIGS. 6A and 6B, ΔF represents the difference in the fluorescence intensity with and without β-lactamases incubation. Data was collected in a 384-well plate with a total volume of 25 µL in each well and shown as an average of three replicate experiments. FIG. 6C illustrates E. coli expressing indicated genes incubated with CDG-1 or CDG-OMe for 3 hours at room temperature and imaged with an IVIS (excitation: 500 nm; emission: 540 nm). FIG. 6D illustrates indicated colony forming units of E. coli expressing TEM-1 Bla and M. tuberculosis var. bovis strain BCG were incubated with CDG-OMe (8 µM) for 20 min and imaged using an IVIS Spectrum. FIG. 6E illustrates detection of M. tuberculosis var. bovis strain BCG with CDG-OMe (2.5 µM) for 7 hours and 18 mins. Data was shown as an average of three replicate experiments (excitation: 490 nm; emission: 530 nm).

FIG. 7A compares the hydrolysis rate of CDC-1 mediated by TEM-1 Bla (0.2 nM). FIG. 7B is the standard curve for fluorescence intensity versus concentration of umbelliferone. FIG. 7C is a Lineweaver-Burke plot of TEM-1 Bla with CDC-1. Error bars indicate the standard deviation of three replicate experiments.

FIG. 8A is a schematic illustration of the hydrolysis of CDC-OMe to release umbelliferone and turn on fluorescence. FIG. 8B illustrates the time course of percentage of hydrolyzed product. FIG. 8C illustrates the spontaneous hydrolysis rate of CDC-OMe. Error bars indicate the standard deviation of triplicate experiments.

DETAILED DESCRIPTION OF THE INVENTION

Figure 1A:
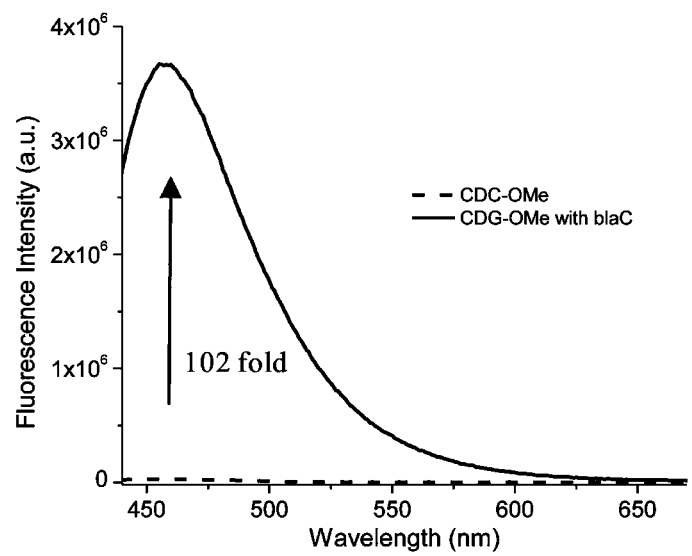
FIGS. 1A-1E compare the kinetics of CDC probes (CDC-1, CDC-3, CDC-OMe, CDC-OEt) with β-lactamases.

The present invention provides β-lactamase substrates and methods for using the substrates to detect β-lactamase and to diagnose tuberculosis. The substrates are useful as probes that can be used in optical methods to detect β-lactamase and to diagnose tuberculosis.

In the compounds of the invention, the cephalosporin backbone serves as a cleavable linker. In certain embodiments, the compounds of the invention include a single moiety (e.g., a chromophore, a luminophore, a fluorophore moiety) that generates an optical signal (absorbance, luminescence, fluorescence) when released from the compound. In one embodiment, the fluorophore is quenched in the intact molecule, and the fluorescence properties of the molecules change upon enzymatic cleavage (e.g., fluorescence increases upon enzyme cleavage). In other embodiments, the compounds of the invention include two moieties (e.g., fluorescent donor and acceptor) and an optical signal (e.g., fluorescence) is generated when released from the compound upon enzyme cleavage.

In one aspect, the invention provides a β-lactamase substrates.

In one embodiment, the invention provides a compound having Formula (I):

Formula (I)

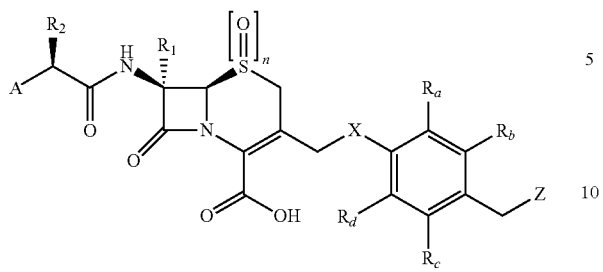

or an ester or a salt thereof.

In another embodiment, the invention provides a compound having Formula (II):

Formula (II)

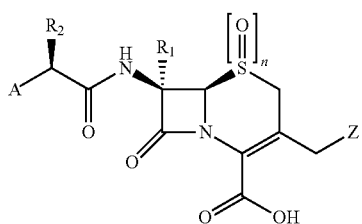

or an ester or a salt thereof.

In Formulas (I) and (II), A is selected from substituted and unsubstituted C6-C10 aryl, and substituted and unsubstituted C3-C7 heteroaryl; $R_1$ is selected from methoxy and ethoxy; $R_2$ is selected from hydrogen, C1-C3 alkyl, C1-C3 alkyl substituted with one or more halogens (e.g., F, Cl, Br), and substituted piperazine; X is O or S; $R_a$, $R_b$, $R_c$, and $R_d$ are independently selected from hydrogen, halogen, nitro, C1-C3 alkyl, C1-C3 alkyl substituted with one or more halogens, C1-C3 alkoxy, and C1-C3 alkoxy substituted with one or more halogens; Z is a reporting group that provides an optical signal when released from the compound; and n is 0 or 1; with the proviso that for Formula (II), when A is phenyl, $R_1$ is methoxy, $R_2$ is hydrogen, and n is 0, Z is not an umbelliferone (7-hydroxycoumarin) moiety.

The compounds of Formulas (I) and (II) include a carboxylic acid group. It will be appreciated that salts and esters of the compounds are also within the scope of the invention. Suitable salts include metal ions (e.g., sodium, potassium, lithium, magnesium, calcium) as well as nitrogen-based cations (e.g., ammonium). Suitable esters include alkyl (e.g., C1-C10), aryl (e.g., C6-C20), and aralkyl (e.g., C6-C20) esters.

In addition to the compounds of Formulas (I) and (II) above in which $R_1$ is methoxy or ethoxy, the present invention also provides parent compounds in which $R_1$ is hydrogen.

In Formulas (I) and (II), A is substituted and unsubstituted C6-C10 aryl or substituted and unsubstituted C3-C7 heteroaryl. Aryl and heteroaryl groups are defined below. These groups may be substituted with halogen, nitro, C1-C3 alkyl, C1-C3 alkyl substituted with one or more halogens, C1-C3 alkoxy, and C1-C3 alkoxy substituted with one or more halogens.

For the compounds of Formulas (I) and (II), in certain embodiments, A is phenyl. In certain embodiments, $R_1$ is methoxy. In certain embodiments, X is O. In certain embodiments, n is 0. In other embodiments, n is 1. In certain embodiments, substituted piperazine is

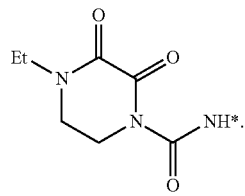

In the compounds of Formulas (I) and (II), Z is a moiety that provides a fluorescent, luminescent, or colorimetric signal when released from the compound. As used herein the phrase "when released from the compound" refers to a product of enzymatic action (β-lactamase) on the compounds of the invention. Enzymatic action cleaves the cephalosporin backbone and releases a product that provides an optical signal thereby signaling cleavage and the presence of the enzyme.

Figure 7A:
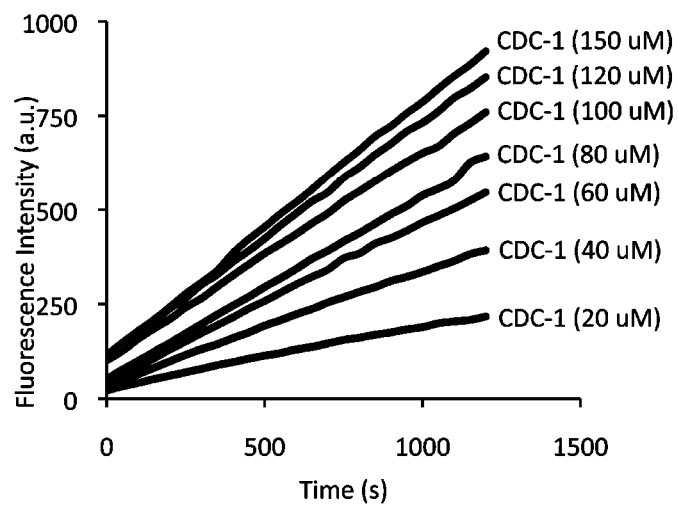
FIGS. 7A-7C compare representative kinetic parameter measurement of beta-lactamase with fluorescent probes (TEM-1 Bla with CDC-1).
Figure 7B:
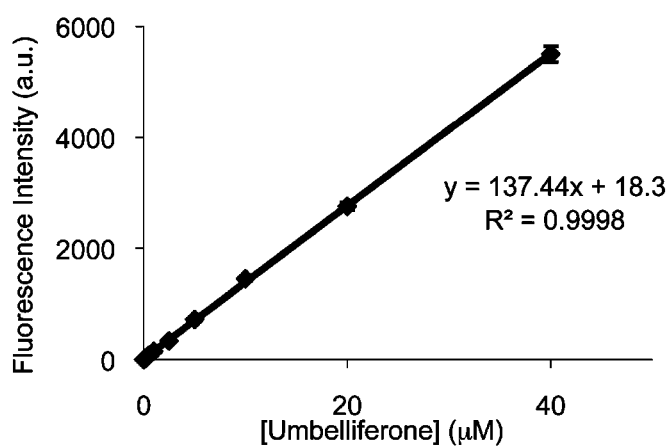
Figure 7C:
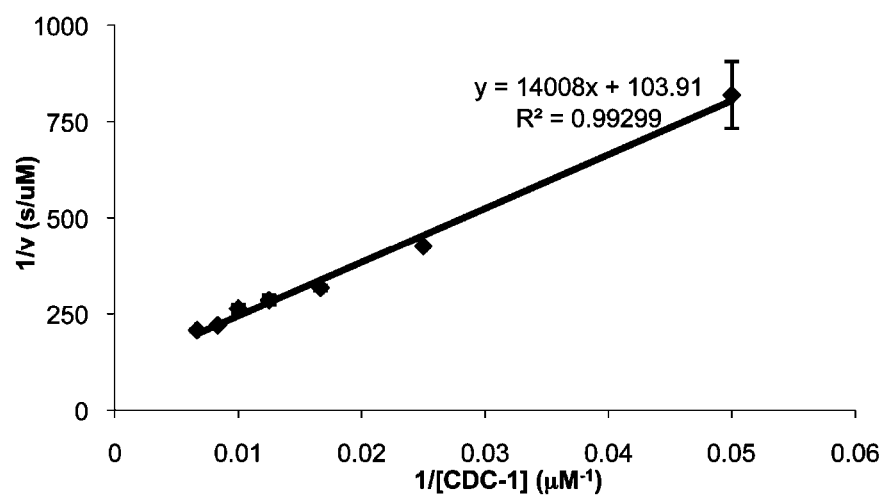

In certain embodiments, Z is a fluorescent moiety. Representative fluorescent moieties useful in the compounds of the invention include those known in the art such as those described in U.S. Pat. No. 7,427,680, U.S. Pat. No. 7,396,926, U.S. Pat. No. 5,955,604, US 2007/0020715, US 2005/0181469, each expressly incorporated herein by reference in its entirety. Representative fluorescent phenolic dyes useful for making the compounds of the invention include those known in the art such as those describes in U.S. Pat. No. 7,427,680 (see, for example, FIG. 7).

In certain embodiments, a chemiluminescence readout can also be generated by use of the adamantylidene-dioxetane. The release of the free phenol from the substrate triggers spontaneous fragmentation of the dioxetane and emission of light. Alternatively, colored or fluorescent precipitates result from the indolyl or 2-(2-hydroxyphenyl) quinazolin-4-one substrates. Release of the free phenol triggers oxidation of 3-hydroxyindoles to blue indigo precipitates. The free 2-(2-hydroxyphenyl) quinazolin-4-one likewise forms a brightly fluorescent precipitate.

As noted above, a variety of fluorescent phenolic dye moieties are useful in making the compounds of the invention (e.g., courmarins, pyrenes, rhodols, and resorufins). In each case the fluorescence is greatly enhanced and shifts to longer wavelengths when the free phenolic group is release from the substrate. Suitable fluorescent moieties include fluorescent phenolic dye moieties such as xanthene moieties. Representative xanthene moieties include fluorescein moieties, rhodol moieties, and rhodamine moieties.

Representative Z groups include courmarin, xanthene, resorufin, cyanine, difluoroboradiazaindacene, bimane, acridine, isoindole, dansyl, aminophthalic hydrazide, aminophthalimide, aminonaphthalimide, quinine, dicyanovinyl, tricyanovinyl, indolaniline, and indamine moieties, and derivatives thereof. As used herein the term "derivatives thereof" refers to substitutions on the named moiety, typically on the ring structure with halogen and lower alkyl groups, that do not significantly alter the moiety's optical properties and that do not significantly alter the compound's substrate properties.

In one embodiment, Z is

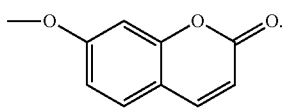

In another embodiment, Z is

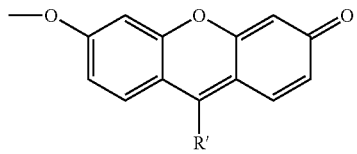

wherein R' is hydrogen or aryl (e.g., phenyl or substituted phenyl). Phenyl substituents include halogen, nitro, C1-C3 alkyl, C1-C3 alkyl substituted with one or more halogens, C1-C3 alkoxy, and C1-C3 alkoxy substituted with one or more halogens.

In a further embodiment, Z is

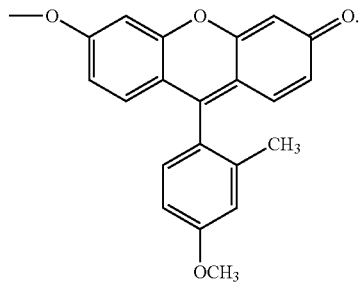 [SMILES: COc1ccc(-c2c3ccc(=O)cc-3oc3cc(OC)ccc23)c(C)c1]

In one embodiment, the invention provides a compound having the formula:

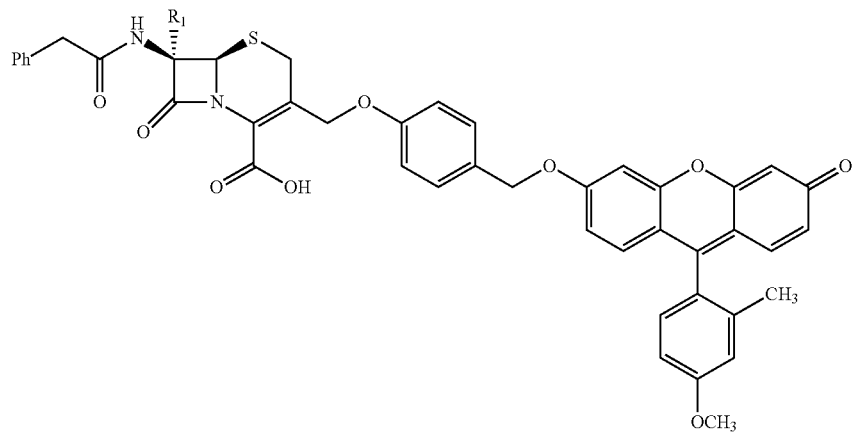

or an ester or a salt thereof, wherein $R_1$ is methoxy.

In another aspect, the invention provides a compound having Formula (III):

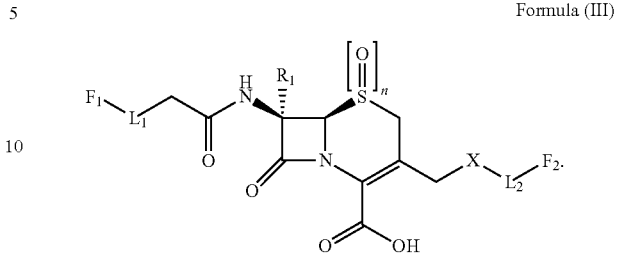

Formula (III)

or an ester or a salt thereof.

For the compounds of Formula (III), $F_1$ and $F_2$ are fluorescent moieties of a FRET pair; $L_1$ is a first linker; $R_1$ is selected from methoxy and ethoxy; n is 0 or 1; X is O or S; and $L_2$ is a second linker.

As used herein, the term "FRET pair" refers to a combination of a fluorescent donor moiety and a quencher moiety. In certain embodiments, $F_1$ is a fluorescent donor moiety and $F_2$ is a quencher moiety. In other embodiments, $F_1$ is a quencher moiety and $F_2$ is a fluorescent donor moiety. Suitable fluorescent donor moieties include indocyanine moieties and derivatives thereof. Representative fluorescent donor moieties include Cy5, Cy5.5, Cy7, and IRDye800 moieties and derivatives thereof. Representative quencher moieties include QSY21, QSY21 disulfonate, QSY22, QSY22 disulfonate, and IRDyeQC-1 moieties and derivatives thereof. As used herein the term "derivatives thereof" refers to substitutions on the named moiety, typically on the ring structure with halogen and lower alkyl groups, that do not significantly alter the moiety's optical properties and that do not significantly alter the compound's substrate properties. FRET, fluorescent donor moieties, and quencher moieties are further described below.

For the compounds of Formula (II), in certain embodiments, $R_1$ is methoxy. In certain embodiments, X is O. In certain embodiments, n is 0.

In the compounds of Formula (III), $L_1$ is a linker for $F_1$ and $L_2$ is a linker for $F_2$. Linkers $L_1$ and $L_2$ serve to attach the fluorescent donor and quencher moieties to the cephalosporin-derived backbone. In certain embodiments, $L_1$ and $L_2$ each independently comprise from 1 to 30 atoms selected from the group consisting of C, N, S, and O atoms. In other embodiments, $L_1$ and $L_2$ each independently comprise from 5 to 20 atoms selected from the group consisting of C, N, S, and O atoms.

$L_1$ and $L_2$ each may independently represent a direct bond to the backbone. Alternatively, suitable linkers for use as $L_1$ and $L_2$ each independently include, but are not limited to, the following: —$(CH_2)_n$—$CONR^2(CH_2)_m$—, —$(CH_2)_n$—$NR^2CO(CH_2)_m$—, —$(CH_2)_n NR^3CONR^2(CH_2)_m$—, —$(CH_2)_n NR^3CSNR^2(CH_2)_m$—, —$(CH_2)_n$—$CONR^3(CH_2)_p CONR^2(CH_2)_m$—, —$(CH_2)_n$—, —$(CH_2)_n$—$NR^3CO(CH_2)_p S(CH_2)_m$—, —$(CH_2)_n S(CH_2)_m$—, —$(CH_2)_n O(CH_2)_m$—, —$(CH_2)_n NR^2(CH_2)_m$—, —$(CH_2)_n SO_2NR^2(CH_2)_m$—, —$(CH_2)_n$—$CO_2(CH_2)_m$—, —$O(CH_2)_n$—, —$S(CH_2)_n$—, —$NR^2(CH_2)_n$—, —$N^+R^2{}_2(CH_2)_n$—, —$OCONR^2(CH_2)_n$—, —$O_2C(CH_2)_n$—, —$SCSNR^2(CH_2)_n$—, —$SCSO(CH_2)_n$—, —$S(CH_2)_n CONR^2(CH_2)_m$—, —$S(CH_2)_n NR^2CO(CH_2)_m$—,

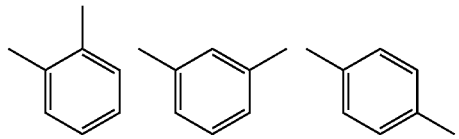

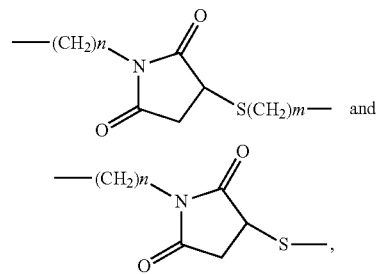

and combinations thereof, wherein $R^2$ is selected from hydrogen and lower alkyl; $R^3$ is selected from hydrogen and lower alkyl; n is 0 or an integer from 1 to 10; and each of m and p is independently 0 or an integer from 1 to 4.

The compounds of Formula (III) include a carboxylic acid group. It will be appreciated that salts and esters of the compounds are also within the scope of the invention. Suitable salts include metal ions (e.g., sodium, potassium, lithium, magnesium, calcium) as well as nitrogen-based cations (e.g., ammonium). Suitable esters include alkyl (e.g., C1-C10), aryl (e.g., C6-C20), and aralkyl (e.g., C6-C20) esters.

In addition to the compounds of Formula (III) above in which $R_1$ is methoxy or ethoxy, the present invention also provides parent compounds in which $R_1$ is hydrogen.

In one embodiment, the invention provides a compound having the formula:

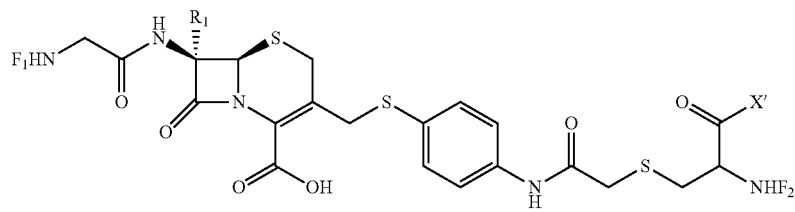

or an ester or a salt thereof,
wherein $R_1$ is methoxy; X' is OH or

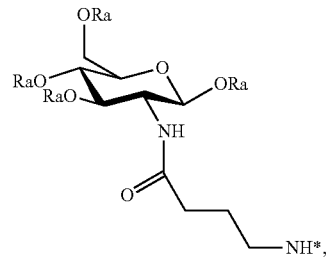

wherein $R_a$ is hydrogen or acetyl;
$F_1$ is

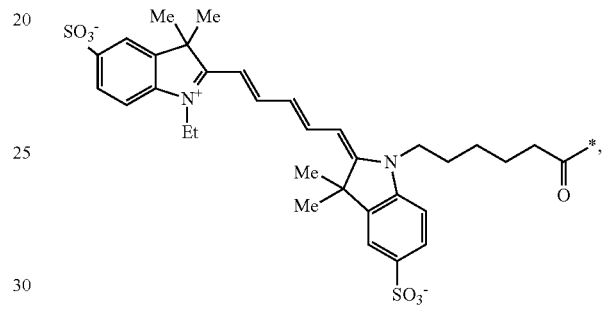

and
$F_2$ is

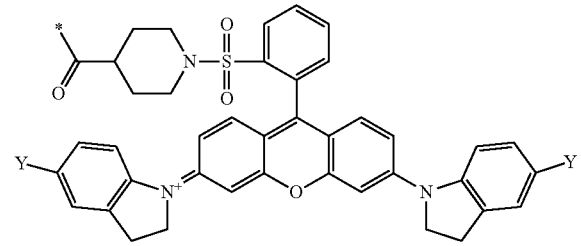

wherein Y is H or $SO_3^-$.

Where the compounds of the invention include two or more fluorophores or chromophores, dyes may be chosen in a manner that one dye absorbs light (quencher or acceptor chromophore) at the wavelength that the other one emits (donor fluorophore). In the intact cephalosporin the two dyes are in close proximity to each other. When exciting the donor fluorophore one observes fluorescence resonance energy transfer (FRET) from the donor to the acceptor instead of donor fluorescence (Forster, T., Ann. Physik 2:55-75 (1948)). If the acceptor is a non-fluorescent dye the energy is given off to the solvent; the donor fluorescence is quenched. In the case of the acceptor being itself a fluorescent dye, fluorescence re-emission occurs at the acceptor's emission wavelength. In polar solvents such as water, hydrophobic donor and acceptor fluorophores can stack when separated by a short flexible linker. Due to this association in the ground state, a dark complex is formed (Yaron, A. et al., Anal. Biochem. 95: 228-235 (1979)). In this complex, neither fluorophore can emit light, causing the fluorescence of both dyes to be quenched (Bojarski, C. and Sienicki, K. Energy transfer and migration in fluorescent solutions. In: Photochemistry and Photophysics, edited by Rabek, J. F. Boca Raton: CRC Press, Inc., 1990, pp. 1-57). In either case, a large change in fluorescence goes along with beta-lactam cleavage, which can be used to measure beta-lactamase activity. As both dyes diffuse away from each other, stacking and energy transfer are disrupted.

Fluorescence resonance energy transfer has been used as a spectroscopic ruler for measuring molecular distances in proteins and peptides as it is effective in the range from 10-100 angstroms. This energy transfer is proportional to the inverse sixth power of the distance between donor and acceptor. Its efficiency is higher, the better donor emission and acceptor absorbance overlap, and the longer the fluorescence lifetime of the donor (in absence of the acceptor). FRET can be very efficient over distances of 10-20 angstroms.

In an embodiment in which the compounds of the invention include multiple fluorophores or chromophores, distances for attachment of donor and acceptor are greater than 10 angstroms and a minimum of 10 bond-lengths, if one includes the two minimal spacers at 7- and 3-positions. Over this distance FRET is very efficient, if the right donor-acceptor pairs are chosen. Upon cleavage, fluorescence increases due to loss of the quencher dye.

In embodiments in which compounds of the invention comprise two or more fluorophores or chromophores. As would readily be appreciated by those skilled in the art, the efficiency of fluorescence resonance energy transfer depends on the fluorescence quantum yield of the donor fluorophore, the donor-acceptor distance and the overlap integral of donor fluorescence emission and acceptor absorption. The energy transfer is most efficient when a donor fluorophore with high fluorescence quantum yield (preferably, one approaching 100%) is paired with an acceptor with a large extinction coefficient at wavelengths coinciding with the emission of the donor. The dependence of fluorescence energy transfer on the above parameters has been reported (Forster, T. (1948) Ann. Physik 2:55-75; Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, Vol 30, ed. Taylor, D. L. & Wang, Y.-L., San Diego: Academic Press (1989), pp. 219-243; Turro, N. J., Modem Molecular Photochemistry, Menlo Part: Benjamin/Cummings Publishing Co., Inc. (1978), pp. 296-361), and tables of spectral overlap integrals are readily available to those working in the field (for example, Berlman, I. B. Energy transfer parameters of aromatic compounds, Academic Press, New York and London (1973)). Cleavage by beta-lactamase relieves quenching and produces an increase in donor fluorescence efficiency. Accordingly, it is apparent that identification of appropriate donor-acceptor pairs for use as taught herein in accordance with the present invention would be essentially routine to one skilled in the art.

The fluorogenic substrates of the invention are typically initially colorless and nonfluorescent outside cells. The substrates are designed so they readily cross cell membranes into the cytoplasm, where they are converted to fluorescent compounds by endogenous nonspecific esterases and stay trapped due to their charges. In the intact molecules, fluorescence energy transfer occurs leading to fluorescence at a particular wavelength when the substrates are excited. Lactamase cleavage of the beta-lactam ring is followed by release of the fluorescent moiety, which release is detectable (e.g., fluorescence may increase with loss of quenching of a single chromophore, or with loss of fluorescence energy transfer where two or more fluorophores are present). Excitation of the release fluorophore now results in fluorescence at a different wavelength or results in an increase in detected fluorescence.

The degree of FRET or amount of fluorescence can be determined by any spectral or fluorescence lifetime characteristic of the excited construct, for example, by determining the intensity of the fluorescent signal from the donor, the intensity of fluorescent signal from the acceptor or quencher, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor. Preferably, changes in the degree of fluorescence or FRET are determined, for example, as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore, the ratio of the two emission intensities is a more robust and preferred measure of cleavage than either intensity alone.

Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. and Wang, Y.-L., San Diego: Academic Press (1989), pp. 219-243; Turro, N. J., Modem Molecular Photochemistry, Menlo Park: Benjamin/Cummings Publishing Col, Inc. (1978), pp. 296-361.

The following are definitions of terms used herein.

The term "alkyl" refers to straight, branched, and cyclic aliphatic groups of 1 to 8 carbon atoms such as from 1 to 6 carbon atoms and 1 to 3 carbon atoms.

The term "aryl" refers to an aromatic group having from six to ten carbon atoms in the aromatic ring. Representative aryl groups include phenyl and naphthyl groups.

The term "heteroaryl" refers to aryl groups that include one or more ring heteroatoms (O, N, S). Representative heteroaryl groups include C5N, C4N, C4O, C4S, C3N2, C3NO, C3N groups (e.g., pyridyl, pyrrolyl, furan, thiophenyl, and imidazolyl groups).

The term "dye" refers to a molecule or part of a compound that absorbs specific frequencies of light, including but not limited to ultraviolet, visible, and near-infrared light. Dyes include phenolic dyes, such as, for example, umbelliferone, fluorescein, and resorufin; aromatic amines, and other compounds, such as, for example, rhodamine. The terms "dye" and "chromophore" are synonymous.

The terms "fluorophore," "fluorescent moiety" refers to a chromophore (light absorbing compound or moiety that fluoresces (emits light upon excitation).

The term "fluorescent donor moiety" refers the radical of a fluorogenic compound which can absorb energy and is capable of transferring the energy to another fluorogenic molecule or part of a compound. Suitable donor fluorogenic molecules include, but are not limited to, coumarins and related dyes; xanthene dyes such as fluoresceins, rhodols, and rhodamines; resorufins; cyanine dyes; bimanes; acridines; isoindoles; dansyl dyes; aminophthalic hydrazides such as luminol and isoluminol derivatives; aminophthalimides; aminonaphthalimides; aminobenzofurans; aminoquinolines; dicyanohydroquinones; and europium and terbium complexes and related compounds. See, for example, chromophores described in US 2007/0020715, pages 10-13, expressly incorporated herein by reference. Accordingly, a donor fluorescent moiety can be a dye or chromophore.

The term "quencher" refers to a chromophoric molecule or part of a compound which is capable of reducing the emission from a fluorescent donor when attached to the donor. Quenching may occur by any of several mechanisms including, for example, quenching of a single fluorophore or chromophore, fluorescence resonance energy transfer between fluorophores and/or chromophores, photoinduced electron transfer, paramagnetic enhancement of intersystem crossing, Dexter exchange coupling, and exciton coupling such as the formation of dark complexes. For example, in a cephalosporin, a fluorophore linked to the cephalosporin may be quenched, and may regain fluorescence upon cleavage of the linker. The term "acceptor" as used herein refers to a quencher which operates via fluorescence resonance energy transfer. Many acceptors can reemit the transferred energy as fluorescence. Examples of moieties that may serve as quencher or acceptor include coumarins and related fluorophores, xanthenes such as fluoresceins, rhodols and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, di- and triphenylmethanes.

Methods of Using the β-Lactamase Substrates

In another aspect of the invention, methods for detecting β-lactamase are provided. In one embodiment, the method includes contacting a sample to be analyzed with substrate of the invention, and measuring an optical signal generated from contacting the sample with the compound (e.g., measuring absorbance, luminescence, chemiluminescence, fluorescence emission intensity). In the method, the measured optical signal is indicative of the presence of β-lactamase in the sample.

In a further aspect of the invention, methods for diagnosing tuberculosis are provided. In one embodiment, the method includes contacting a sample to be analyzed with substrate of the invention, and measuring an optical signal generated from contacting the sample with the compound (e.g., measuring absorbance, luminescence, chemiluminescence, fluorescence emission intensity). In the method, the measured optical signal (e.g., fluorescence emission intensity) is indicative of the presence of tuberculosis in the sample.

In the methods noted above, suitable samples include sputum, pleural fluid, spinal fluid, blood, urine, saliva, stool, tissue biopsies, tissue homogenates, directly in live animals or human patients, or a sample obtained by swabbing an area of interest on a subject.

Suitable samples for analysis by the methods of the invention can include a pathogenic bacterial species that express beta-lactamase or another enzyme that a similar fluorogenic probe can be produced for such as *Bacteroides, Clostridium, Streptococcus, Staphylococcus, Pseudomonas, Haemophilus, Legionella, Mycobacterium, Escherichia, Salmonella, Shigella,* or *Listeria*.

In certain embodiments, measuring fluorescence emission intensity comprises exciting the sample with light having a wavelength in the range from about 300 nm to about 900 nm. In other embodiments, wherein measuring fluorescence emission intensity comprises exciting the sample with light having a wavelength in the range from about 540 nm to about 730 nm.

In certain embodiments, measuring fluorescence emission intensity comprises measuring emission at a wavelength in the range from about 300 nm to about 900 nm. In other embodiments, measuring fluorescence emission intensity comprises measuring emission at a wavelength in the range from about 650 nm to about 800 nm.

The preparation of representative substrates of the invention are described in Examples 2 (CDC family) and 3 (CDG family).

Clinical testing using a representative β-lactamase substrate of the invention (CDG-OMe) is described in Example 4.

The following is a description of the preparation and use of representative β-lactamase substrates of the invention.

One of the critical needs for improving diagnosis of tuberculosis is identification of accurate biomarkers for active Mtb. Recently the trehalose mycolyltransferase enzymes have been utilized to incorporate unnatural trehalose analogs into *Mycobacterium tuberculosis* for Mtb detection. Because it requires cell culturing for the probe incorporation, the process can take long time due to the slow growth rate of Mtb. BlaC has the potential to serve and has many advantages as a diagnostic marker. All tuberculosis complex bacteria examined display strong β-lactamase-dependent signal, including BCG, tuberculosis laboratory strains and tuberculosis clinical isolates, totaling more than 20 different strains. In addition, complete genome sequencing of more than 54 Mtb strains from numerous geographical regions, MDR and XDR strains, demonstrate that BlaC is highly conserved in all Mtb clinical isolates, with only 2 non-synonymous single-nucleotide changes that would still produce an active enzyme. These observations are consistent with observations in the literature that indicate 100% (18 for *M. tuberculosis,* 9 for *M. bovis,* 5 for *M. africanum* and 17 for *M. kansasii*) of the strains within the tuberculosis complex produce β-lactamase and are positive for enzymatic activity. Because BlaC is an enzyme, its activity promises great sensitivity for detection of tubercle bacilli with fluorogenic substrates. However, previously available probes lack specificity for BlaC13, allowing activation by other lactamases, such as the common TEM-1 Bla found in Gram-negative bacteria 27, 28, which would reduce their accuracy for tuberculosis diagnosis.

Extensive research has been devoted to β-lactamases because of their role in rendering bacteria resistant to lactam antibiotics. However, most previous studies focus on designing molecules that are poor β-lactamase substrates, in contrast to the present invention, providing substrate probes that have rapid kinetics and are selective for BlaC. The unique substrate specificity loop of BlaC was exploited to design BlaC specific fluorogenic substrates. The replacement of R164 in TEM-1 Bla by Ala results in the loss of stabilizing salt bridges in BlaC, ultimately increasing the flexibility of the BlaC substrate specificity loop. Therefore, the active site of BlaC more likely accommodates chemical modifications on the lactam structure. Based on this structural insight, substitutions at the 7-C position of the lactam ring, which is readily accessible to chemical synthesis, were explored. The introduced methoxy group is well accommodated in the pocket of BlaC, as revealed by the solved acyl-intermediate structural complex.

CDC-OMe showed excellent selectivity for BlaC over TEM-1 Bla, but its catalytic efficiency for BlaC is low (the value of $k_{cat}/K_M$ is $2.1\times10^4\ s^{-1}M^{-1}$), which requires long co-incubation times for a positive result and, thus, compromises its sensitivity for Mtb detection. Further modification of the structure of the substrate at the 3' position by replacing the fluorophore coumarin with a benzyl ether linkage led to a much improved fluorogenic BlaC substrate probe CDG-OMe whose $k_{cat}/K_m$ increases by 11-fold to $2.4\times10^5\ s^{-1}M^{-1}$ in PBS while maintaining high stability and selectivity for BlaC over TEM-1 Bla. The use of the green fluorophore further enhanced its sensitivity for detecting live mycobacteria in solution.

An ideal Mtb probe should be able to detect a single tubercle *bacillus* within minutes. CDG-OMe currently can detect $2\times10^5$ BCG within 20 min, and $10^3$ BCG with 7 hours incubation. It has been shown that nanotechnology can drastically improve the sensitivity of detection for enzymatic assays by decreasing the reaction volume. With an appropriately designed nano device, rapid, selective detection of single Mtb in clinical samples, such as patient's sputum, based on BlaC and CDG-OMe should be feasible, and would substantially contribute to decrease Mtb-associated death rates and disease transmission.

The present invention provides a series of fluorogenic probes specific for Mtb by taking advantage of the uniquely flexible substrate specificity loop of the BlaC enzyme expressed by tubercle bacilli. These probes are chemically modified cephalosporin lactams with a 7α-methoxy substitution. The acyl intermediate complex of the E166A BlaC mutant and the probe has been successfully co-crystallized and the X-ray structure has been solved for the first time at the resolution of 2.3 Å, which reveals structural insights into the observed specificity of the probes for BlaC over TEM-1 Bla. A refined green fluorescent probe CDG-OMe has enabled successful detection and imaging of intact BCG in culture, and is promising for clinical diagnosis of Mtb in patient sputum and other diagnostic specimens.

In one aspect, the invention provides cephalosporin-based fluorogenic substrates that enable sensitive detection of Mtb and *bacillus* Calmette-Guérin (BCG) in vitro and in living mice. The invention provides a series of rationally designed fluorescent probes based on chemically modified cephalosporin lactams by taking advantage of the unique flexibility of the BlaC substrate specificity loop. Both enzymatic kinetic measurement and structural analyses confirmed that the designed probes display specificity for BlaC over its close class A homologue TEM-1 Bla. A refined green fluorescent probe with high specificity and sensitivity for BlaC as well as high chemical stability enabled successful detection and imaging of intact BCG in culture. This BlaC-specific probe has potential for clinical diagnosis of Mtb in patient sputum and other diagnostic specimens.

Design of BlaC-Specific Fluorogenic Probes

Class A β-lactamases are capable of hydrolyzing all classes of β-lactam substrates, albeit with differential specificity. Substrate specificity of β-lactamases is conferred by Ambler residues (163-178) comprising the omega loop, or substrate specificity loop and is partially dependent upon the ability of the catalytic base, E166, to assume the optimal conformation for hydrolytic water coordination and deacylation. The cephalosporin substrates of the invention are specific for Mtb BlaC over other class A β-lactamases, such as TEM-1 Bla, and achieve specific detection of Mtb. The unique flexibility of the BlaC substrate specificity loop was the feature exploited for designing specificity of the substrates of the invention. A Mtb BlaC-specific cephalosporin will displace the substrate specificity loop, but the flexibility of the loop will facilitate the coordination of E166 for deacylation. The same substrate will not be turned over as efficiently by β-lactamases with a more rigid loop (such as TEM-1 Bla) because E166 will not be able to assume the necessary conformation for substrate deacylation and turnover. Therefore, the introduction of bulky substitutions on the lactam take advantage of the flexibility of the substrate specificity loop of BlaC and result in improved specificity for Mtb BlaC. Modification of the cephalosporin scaffold at the 3' and 7' positions is chemically facile, and serves as a starting point for the generation of multiple variants that may be specific to Mtb BlaC.

The general structure of blue fluorescent probes and their hydrolysis by β-lactamase, which triggers the release of umbelliferone and turns on fluorescence is shown in Scheme 1.

Scheme 1.

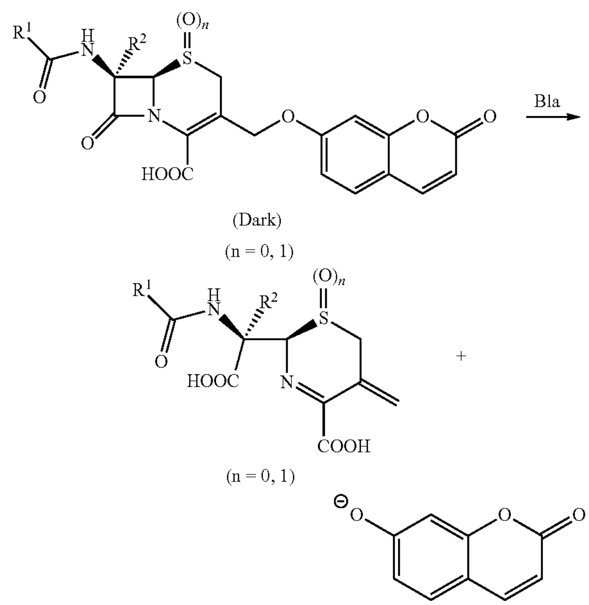

(Dark)

(n = 0, 1)

+

(n = 0, 1)

Umbelliferone
(Strong blue fluorescent)

$R^1$ = Bn, $R^2$ = H, n = 0 CDC-1
$R^1$ = Bn, $R^2$ = H, n = 1 CDC-2

$R^1$ =

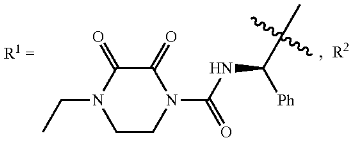

, $R^2$ = H, n = 0 CDC-3

$R^1$ = Bn, $R^2$ = OMe, n = 0 CDC-OMe
$R^1$ = Bn, $R^2$ = OEt, n = 0 CDC-OEt
$R^1$ = Me, $R^2$ = H, n = 0 CDC-4
$R^1$ = Me, $R^2$ = OMe, n = 0 CDC-5

A series of fluorescent probes with substitutions on the side chain ($R^1$) of the 7-amino group or the 7-position of the lactam ring ($R^2$) (Scheme 1). Each probe contains the alkylated umbelliferone at the 3'-position and initially fluoresces little when excited at 400 nm. These substituted substrates are readily hydrolyzed by BlaC and release free fluorophore to turn on fluorescence, but their hydrolysis by TEM-1 Bla proceeds with much slower kinetics. These blue fluorescent probes were synthesized as outlined in Scheme 2 (CDC-1 and CDC-OMe).

C., 1 h, 45% from 1; (f) DCM/TFA/TIPS/$H_2$O (50/45/2.5/2.5), 5 min, rt, 80%; (g) tBuOCl, LiOMe, THF, MeOH, −78° C., 0.5 h, 73%; and (h) DCM/TFA/TIPS/$H_2$O (50/45/2.5/2.5), 5 min, rt, 84%.

The alkylation of umbelliferone in the presence of potassium carbonate initially led to a mixture of isomers with an isomerized $\Delta 3$ double bond, but treatment with meta-chloroperoxybenzoic acid (mCPBA) and subsequent reduction afforded a single 3-double bond isomer. The key methoxylation step of the protected lactam ester was carried out

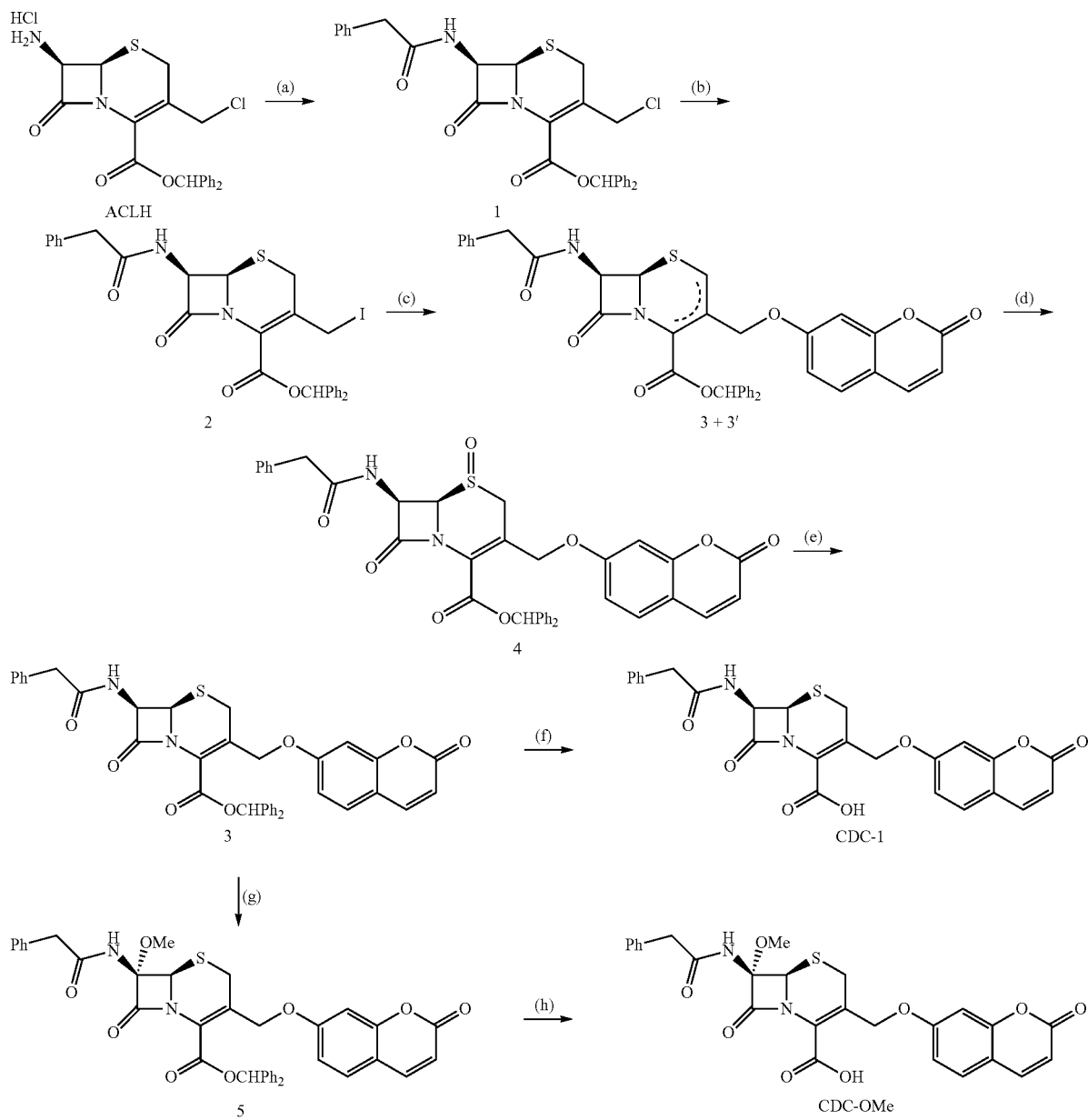

Scheme 2.

Scheme 2 is a schematic illustration of the preparation of two probes (CDC-1 and CDC-OMe): (a) PhCH$_2$COCl, TEA, 2,6-lutidine, CH$_3$CN, rt, overnight, 97%; (b) NaI, acetone, rt, 1 h; (c) 7-hydroxycoumarin, K$_2$CO$_3$, CH$_3$CN, rt, 2.5 h; (d) mCPBA, DCM, 0° C., 0.5 h; (e) NaI, TFAA, acetone, 0° following the reported procedure by using LiOMe and tBuOCl, resulting in the desired 7α-methoxy product with a good yield. The preparation and characterization of representative probes of the invention are described in the Examples.

Enzymatic Kinetics for Mtb BlaC and TEM-1 Bla

Figure 1B:
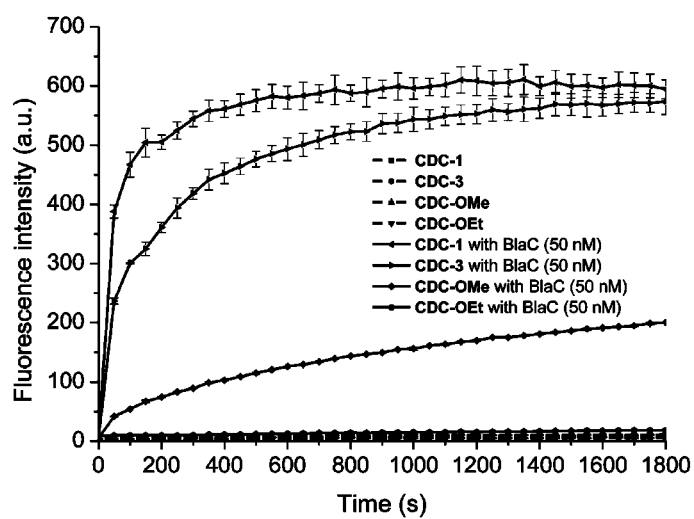
Figure 1C:
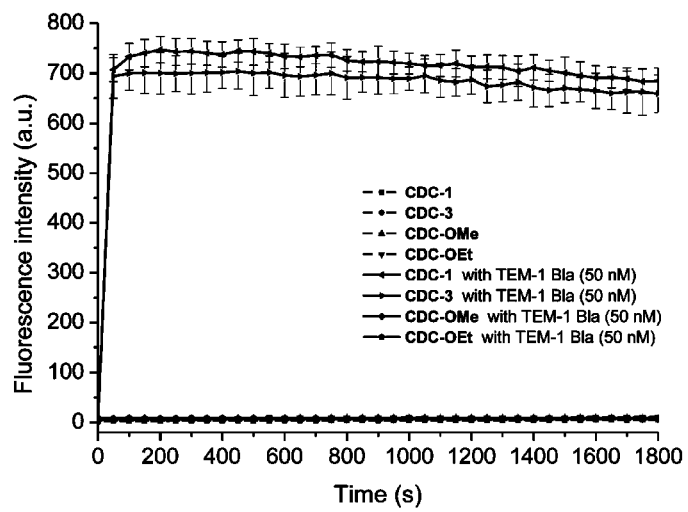

The fluorescent spectra of the probes CDC-1, CDC-3, CDC-OMe and CDC-OEt were recorded before and after BlaC treatment to examine their responses to BlaC. With excitation at 400 nm, all probes exhibited over a 100-fold increase in the fluorescence intensity at 455 nm after incubation with BlaC (FIG. 1A), but their reaction rates varied significantly (FIG. 1B): under the same conditions, the hydrolytic rate by BlaC decreases in the order of CDC-1>CDC-3>CDC-OMe>CDC-OEt which appears to correlate with the size of the $R^2$ group. CDC-OMe showed more than 30-fold enhancement of fluorescence intensity in less than 30 minutes. The larger substitution (ethoxy vs. methoxy) provided CDC-OEt with only slight fluorescence enhancement within 30 minutes. On the other hand, the same concentration of TEM-1 Bla (50 nM) gave no change in the fluorescence intensity in 30 minutes (FIG. 1C) with CDC-OMe, while producing rapid fluorescence with CDC-1 and CDC-3. These results demonstrate that CDC-OMe can preferentially detect BlaC over TEM-1 Bla.

Figure 1D:
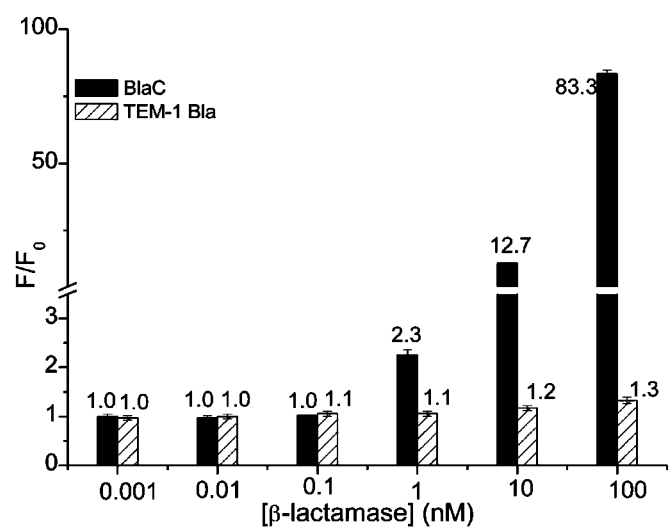
Figure 1E:
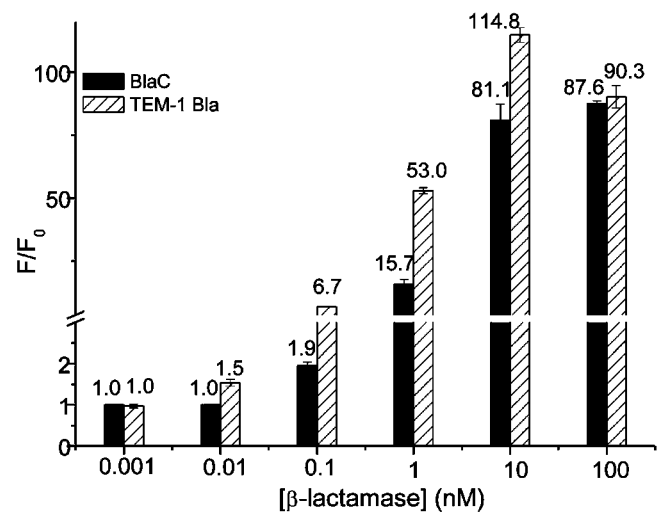

The response of CDC-OMe to varying concentrations of BlaC and TEM-1 Bla (at a range of 1 pM to 100 nM) was examined to investigate its specificity (FIG. 1C). 1 nM of BlaC (100 μL) induced a 130% increase in the fluorescence intensity within one hour ($F/F_0=2.3$), while a 100-fold higher TEM-1 Bla concentration (100 nM) could only produce 30% fluorescence enhancement ($F/F_0=1.3$). In contrast, CDC-1 incubated with TEM-1 Bla generates stronger signal than with BlaC (FIG. 1d) indicating its preference for TEM-1 Bla.

The kinetic parameters of fluorescent probes BlaC and TEM-1 Bla, including catalytic constant $k_{cat}$ and Michaelis constant $K_m$, are obtained from Linweaver-Burk plots (FIGS. 7A-7C) and summarized in Table 1.

Consistent with the above observations, the kinetic efficiency ($k_{cat}/K_m$) of CDC-OMe for BlaC is $2.1 \times 10^4$ s$^{-1}$M$^{-1}$, over 1,000 times higher than that for TEM-1 Bla (15.2 s$^{-1}$M$^{-1}$). When an ethoxy group is introduced at the 7-position (CDC-OEt), no hydrolysis by TEM-1 Bla was detected, and the value of $k_{cat}/K_m$ by BlaC decreases substantially to $1.9 \times 10^2$ s$^{-1}$M$^{-1}$.

Additional structural modifications have been explored for their effects on the enzymatic kinetics of BlaC and TEM-1 Bla. Probes with a large substitution group on the 7-amine position ($R^1$) such as CDC-3 display higher catalytic efficiency for TEM-1 Bla ($1.3 \times 10^6$ s$^{-1}$M$^{-1}$) than for BlaC ($8.7 \times 10^4$ s$^{-1}$M$^{-1}$). On the other hand, substitution by phenylacetyl or acetyl groups (e.g., CDC-1, CDC-4) at this position results in only a slight difference in the catalytic efficiency between BlaC and TEM-1 Bla (CDC-1: $2.1 \times 10^5$ versus $3.6 \times 10^5$ s$^{-1}$M$^{-1}$; CDC-4: $6.8 \times 10^4$ versus $7.5 \times 10^4$ s$^{-1}$M$^{-1}$, respectively). Oxidation of the sulfur into sulfoxide (CDC-2) causes a decrease in the kinetic efficiency for both BlaC and TEM-1 Bla.

Combining the results from the kinetic analysis of synthesized fluorescent probes, it can be deduced that a BlaC-preferred probe would possess (1) a relatively small $R^2$ substitution group, (2) a medium size substitution group at the 7-amino position such as phenylacetyl group, and (3) no oxidation of its sulfur. As an example of this type of structure, CDC-OMe shows over 1,000-fold higher catalytic efficiency for BlaC over TEM-1 Bla.

Crystal Structure Analysis

To understand the structural origin of the observed specificity of CDC-OMe for BlaC, X-ray crystallographic structural studies were performed by obtaining the acyl intermediate complex structures of CDC-OMe and CDC-1 with BlaC. The interactions of these same compounds with TEM-1 Bla was modeled.

Differential Flexibility of BlaC and TEM-1 Bla Substrate Specificity Loops.

Figure 2A:
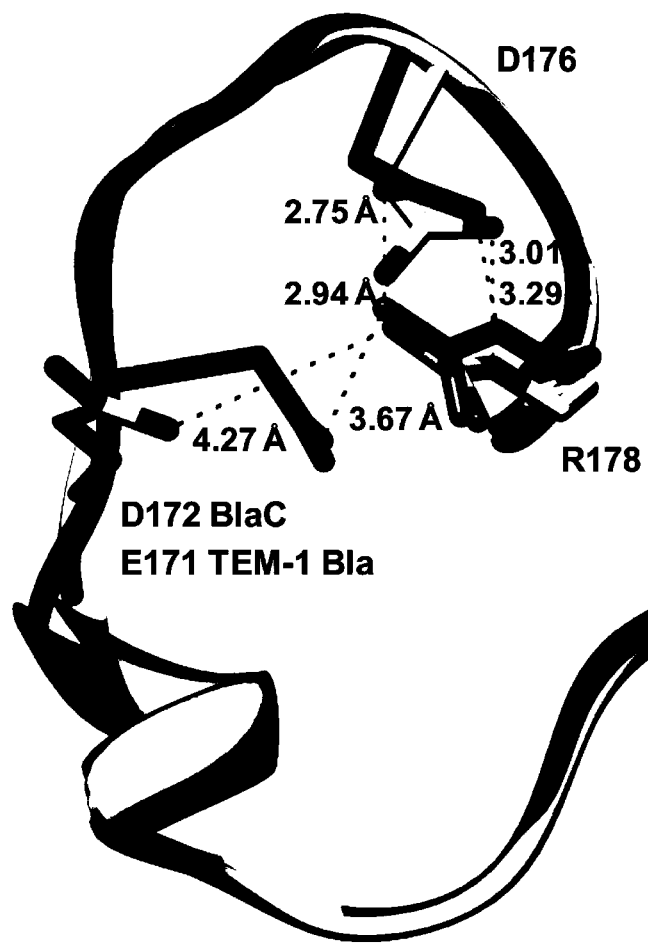
FIGS. 2A and 2B illustrate the superimposition of BlaC (2GDN, shaded) and TEM-1 Bla (1M40, white) substrate specificity loops (residues 163-179).

The substrate specificity loops of *E. coli* TEM-1 Bla and Mtb BlaC share 67% sequence identity over 20 residues (160-180). Conserved salt bridges in both enzymes formed by D172-R178 and D176-R178 stabilize the loop conformers of the unoccupied active sites (FIG. 2A).

Figure 2B:
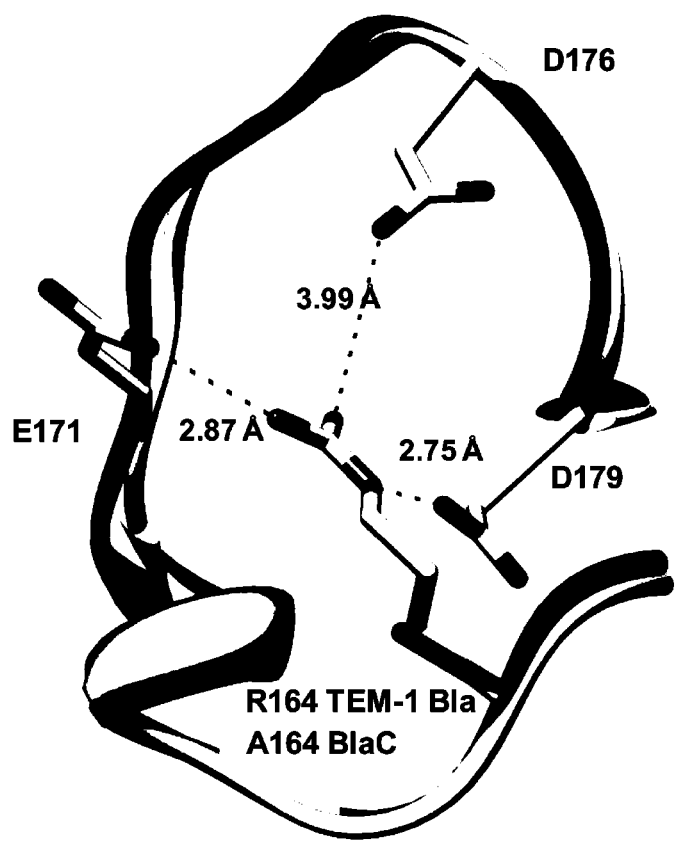

The largest phenotypic difference between the two enzymes is due to residue 164, which is an arginine in TEM-1 Bla and an alanine in BlaC. R164 plays a central role in the molecular dynamics of the substrate specificity loop in TEM-1 Bla. The R164 guanidinium side chain nitrogens (Nε, NH, and NH$_2$) stabilize a triad of carboxylates formed from D176, D179, and E171 side chains with electrostatic interaction distances of 2.87 Å, 3.99 Å, and 2.75 Å, respectively. R164 forms three additional salt bridges that stabilize the TEM-1 Bla substrate specificity loop relative to BlaC (FIG. 2B).

A164 prevents the formation of the additional stabilizing salt bridges in BlaC, ultimately increasing the flexibility of the BlaC substrate specificity loop relative to TEM-1 Bla.

TABLE 1

Kinetic Parameters of Fluorescent Probes for BlaC and TEM-1 Bla[a]

| Name | BlaC | | | TEM-1 Bla | | | Spontaneous Hydrolysis Rate (s$^{-1}$) |
|---|---|---|---|---|---|---|---|
| | $K_m$ (μM) | $k_{cat}$ (s$^{-1}$) | $k_{cat}/K_m$ (s$^{-1}$M$^{-1}$) | $K_m$ (μM) | $k_{cat}$ (s$^{-1}$) | $k_{cat}/K_m$ (s$^{-1}$M$^{-1}$) | |
| CDC-1 | 63 | 13 | $2.1 \times 10^5$ | 135 | 48 | $3.6 \times 10^5$ | $2 \times 10^{-7}$ |
| CDC-2 | 136 | 0.51 | $3.8 \times 10^3$ | 454 | 7 | $1.5 \times 10^4$ | $1 \times 10^{-7}$ |
| CDC-3 | 69 | 6 | $8.7 \times 10^4$ | 59 | 77 | $1.3 \times 10^6$ | $2 \times 10^{-7}$ |
| CDC-OMe | 47 | 1 | $2.1 \times 10^4$ | 50 | $7.6 \times 10^{-4}$ | 15.2 | $3 \times 10^{-7}$ |
| CDC-OEt | 131 | 0.026 | $1.9 \times 10^2$ | ND[b] | ND[b] | ND[b] | $2 \times 10^{-7}$ |
| CDC-4 | 148 | 10 | $6.8 \times 10^4$ | 133 | 10 | $7.5 \times 10^4$ | $2 \times 10^{-7}$ |
| CDC-5 | 139 | 0.52 | $3.7 \times 10^3$ | ND[b] | ND[b] | ND[b] | $3 \times 10^{-7}$ |
| CDG-1 | 2.1 | 3.7 | $1.8 \times 10^6$ | 1.0 | 8.7 | $8.7 \times 10^6$ | $3 \times 10^{-7}$ |
| | (2.1)[c] | (1.0) | $(4.8 \times 10^5)$ | (1.9) | (5.2) | $(2.7 \times 10^6)$ | $(6 \times 10^{-7})$[c] |
| CDG-OMe | 2.9 | 0.7 | $2.4 \times 10^5$ | 30 | $1.1 \times 10^{-3}$ | 37 | $3 \times 10^{-7}$ |
| | (4.7)[c] | (0.8) | $(1.7 \times 10^5)$ | (40) | $(6.7 \times 10^{-4})$ | (17) | $(2 \times 10^{-7})$[c] |

[a]Kinetic data were measured in PBS buffer (1x, pH = 7.4) at room temperature (22° C.) unless otherwise noted. All data indicate averages of three replicate experiments.
[b]Not Determined due to extremely slow kinetics.
[c]Data in parentheses were measured in MES buffer (0.1M, pH 6.6) at 22° C.

The increased flexibility is underscored by B-factors for residues surrounding E166 (164-168), which are 108% of the mean B-factor in BlaC, and 87% of the mean B-factor of TEM-1 Bla. The structural plasticity of these residues allows the catalytic base E166 to sample multiple conformations and increases the capability of BlaC to hydrolyze substrates in the acyl-intermediate state. The precise location of atoms participating in electrostatic interactions, including salt bridges has previously been suggested to confer substrate specificity.

The Role of the Methoxy Modification.

Figure 3A:
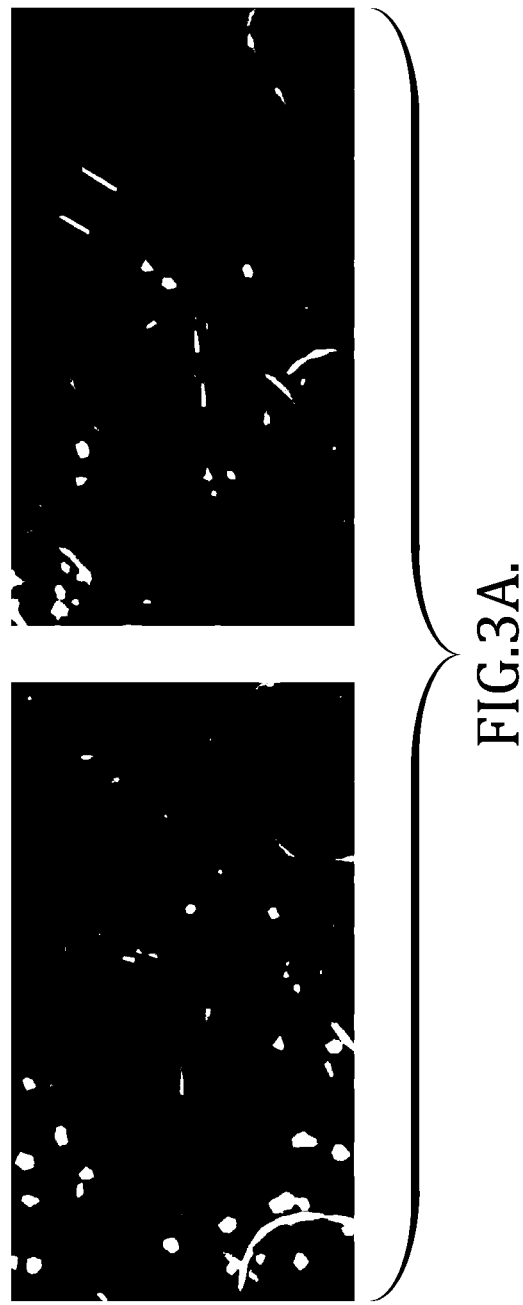
FIGS. 3A-3C illustrate active site details of BlaC-CDC-OMe (left) and BlaC-CDC-1 (right) acyl-intermediate complexes.
Figure 3B:
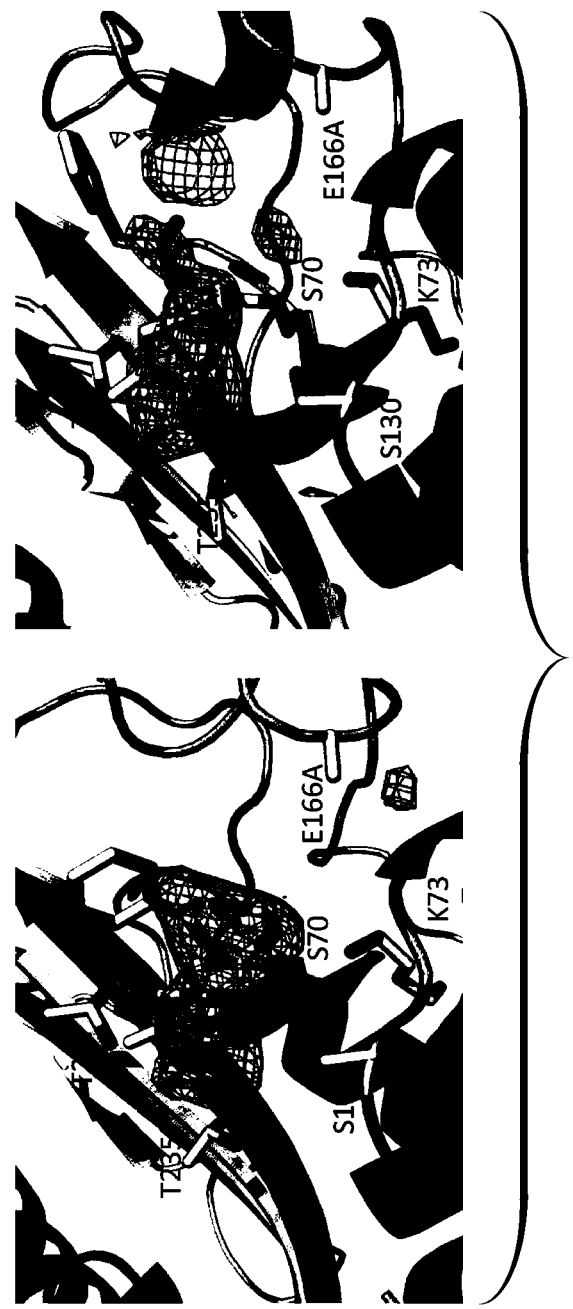
Figure 3C:
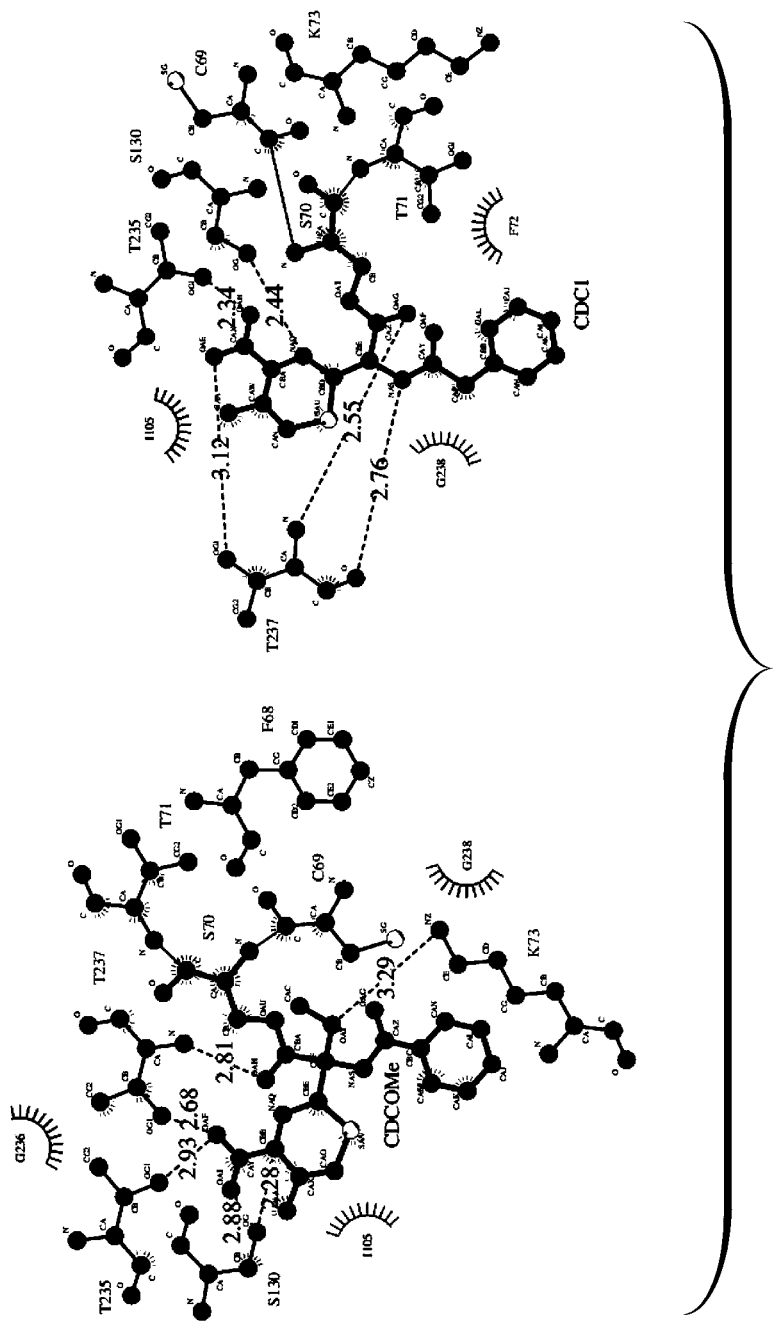

CDC-1 and CDC-OMe have in common a phenylacetylamino side chain but differ by the presence of a methoxy group in CDC-OMe characteristic of cephamycins. Addition of the methoxy group to CDC-1 to form CDC-OMe resulted in decreased BlaC turnover ($k_{cat}$) from 13 $s^{-1}$ to 1 $s^{-1}$ and specificity ($k_{cat}/K_m$) from $2.1 \times 10^5$ $s^{-1}M^{-1}$ to $2.1 \times 10^4$ $s^{-1}M^{-1}$, respectively (Table 1). The observed difference in kinetic parameters can be explained by the acyl-intermediate complex crystal structures of BlaC-CDC-1 and BlaC-CDC-OMe. The acyl-intermediates exist in similar orientations, and share conserved electrostatic interactions with substrate recognition residues T235, T237, S130, and S70 (FIG. 3C). The phenyl groups in both CDC-1 and CDC-OMe are disordered due to the lack of active site contacts and facing open to the solvent. In contrast, CDC-1 makes a unique 2.76 Å electrostatic interaction with the backbone carbonyl oxygen of T237. The methoxy group of CDC-OMe forms an electrostatic interaction with the side chain amino group of K73, and sterically constrains the orientation of the CDC-OMe 7'-phenylacetylamino substituent, which is rotated approximately 90° relative to the CDC-1 acyl intermediate. The CDC-OMe-K73 interaction positions the methoxy group directly in the path between the acyl bond and catalytic residue E166, which is required to complete the hydrolysis reaction. Therefore, the methoxy group of CDC-OMe hinders turnover by directly interfering with hydrolytic water coordination by E166 required for deacylation (FIGS. 3A-3C). Replacement of the methoxy group with a bulkier ethoxy group (CDC-OEt) causes more serious occlusion, which is consistent with a further 40-fold reduction in turnover number (Table 1).

Figure 4A:
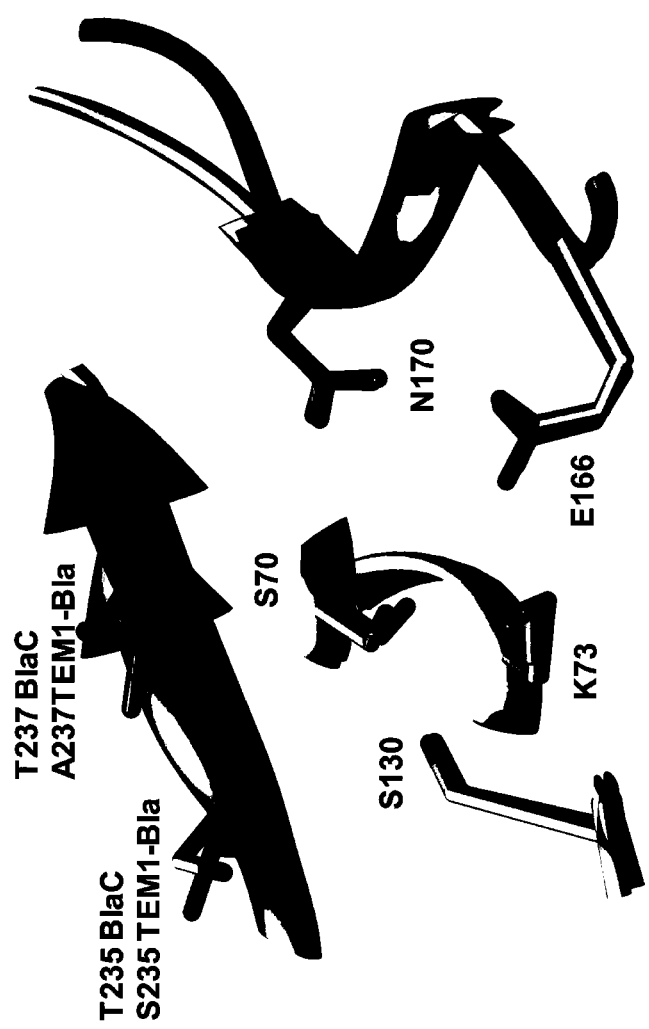
FIGS. 4A and 4B compare TEM-1 Bla (white) and BlaC (shaded) active sites.
Figure 4B:
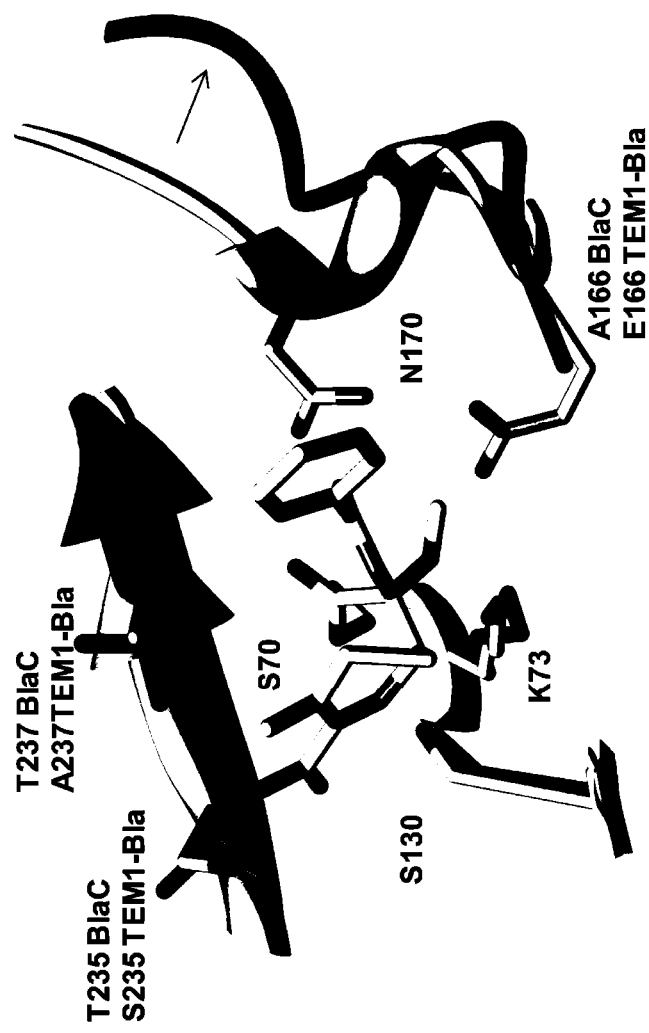

The difference in flexibility between the BlaC and TEM-1 Bla substrate specificity loops maximizes the specificity of CDC-OMe for BlaC over TEM-1 Bla. The rigid TEM-1 Bla substrate specificity loop, primarily attributed to R164, restricts the conformational sampling of E166 resulting in decreased turnover of CDC-OMe relative to BlaC. The BlaC A164 prevents formation of stabilizing electrostatic interactions within the loop (FIGS. 4A and 4B), and is responsible for the increased flexibility of the BlaC substrate specificity loop relative to TEM-1 Bla. The flexibility of the BlaC substrate specificity loop facilitates the optimal positioning of E166 for CDC-OMe deacylation, and confers specificity of CDC-OMe for BlaC over TEM-1 Bla.

Detection and Imaging of Live Mycobacteria

Figure 5A:
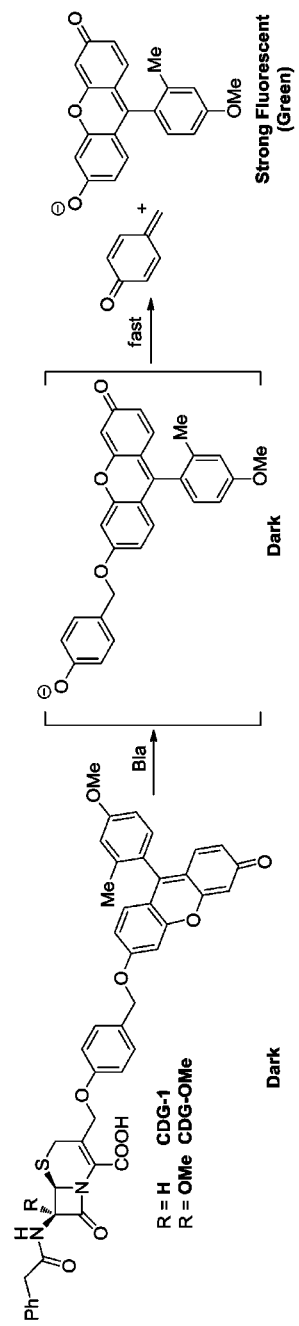
FIGS. 5A-5E compare β-lactamase selectivity of fluorescent substrates CDG-1 and CDG-OMe.
Figure 8A:
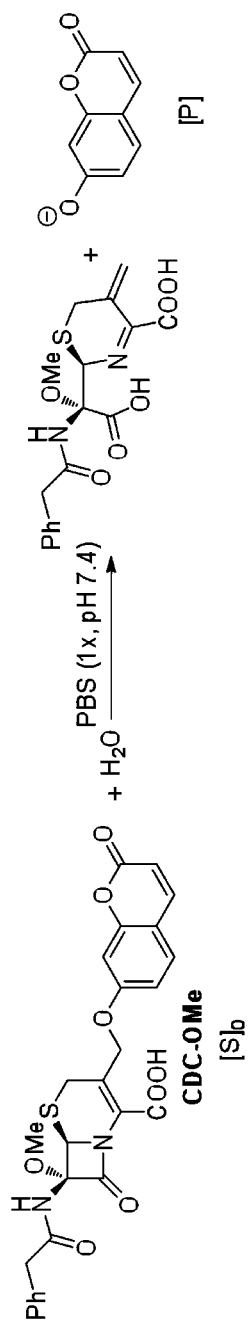
FIGS. 8A-8C illustrate the spontaneous hydrolysis of CDC-OMe in buffer.
Figure 8B:
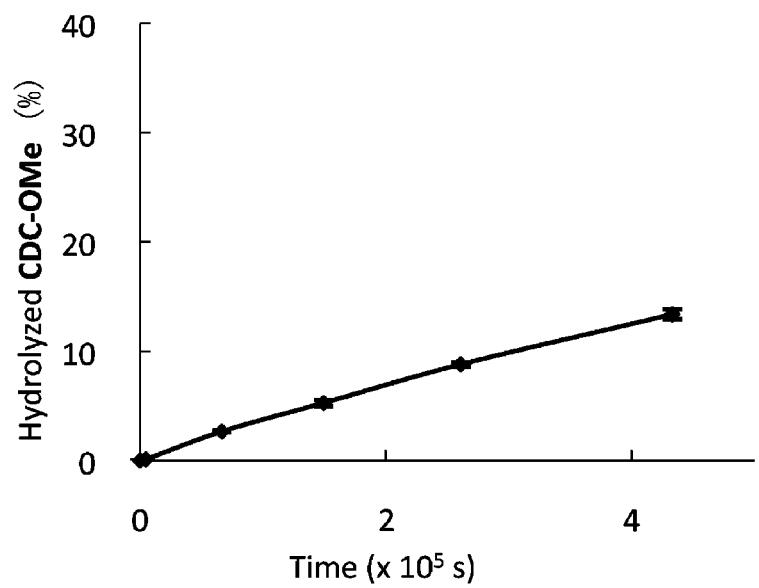

CDC-OMe shows over 1,000-fold higher catalytic efficiency for BlaC than for TEM-1 Bla, and has a spontaneous hydrolysis rate constant in PBS (pH 7.4) of $3.3 \times 10^{-7}$ $s^{-1}$ (FIGS. 8A-8C), which makes it attractive for sensitive detection of *M. tuberculosis* in clinical specimens. The feasibility of CDC-OMe for detection of BlaC expressed by *E. coli* was evaluated. CDC-OMe was incubated with the same number of *E. coli* expressing no β-lactamase, TEM-1 Bla or BlaC (FIG. 9) for 2 hours and strong fluorescence was observed only with *E. coli* expressing BlaC. As a control, the fluorescence for CDC-1 was present in *E. coli* expressing either TEM-1 Bla or BlaC. This result demonstrates that CDC-OMe can specifically detect BlaC in intact *E. coli*. However, the sensitivity for detecting BlaC expressed by *M. tuberculosis* var. *Bovis* strain BCG is low due to the high background of BCG at the excitation and emission wavelengths of the blue fluorophore umbelliferone. Therefore, umbelliferone was replaced with the green fluorescent dye TOKYO GREEN® (FIG. 5A). TOKYO GREEN® allows stable single-site attachment at its phenolic position, but the direct coupling product with cephalosporin at the 3'-position, similar to CDC probes, displayed 21-fold less stability (with a spontaneous hydrolysis rate of $7 \times 10^{-6}$ $s^{-1}$ in PBS) than CDC-OMe. A benzyl ether linker was thus introduced between the 3'-position of the lactam and TOKYO GREEN® to increase its stability (FIG. 5A). The syntheses of green fluorogenic substrates CDG-1 and CDG-OMe are outlined in Scheme 3, which is similar to that of the CDC probes.

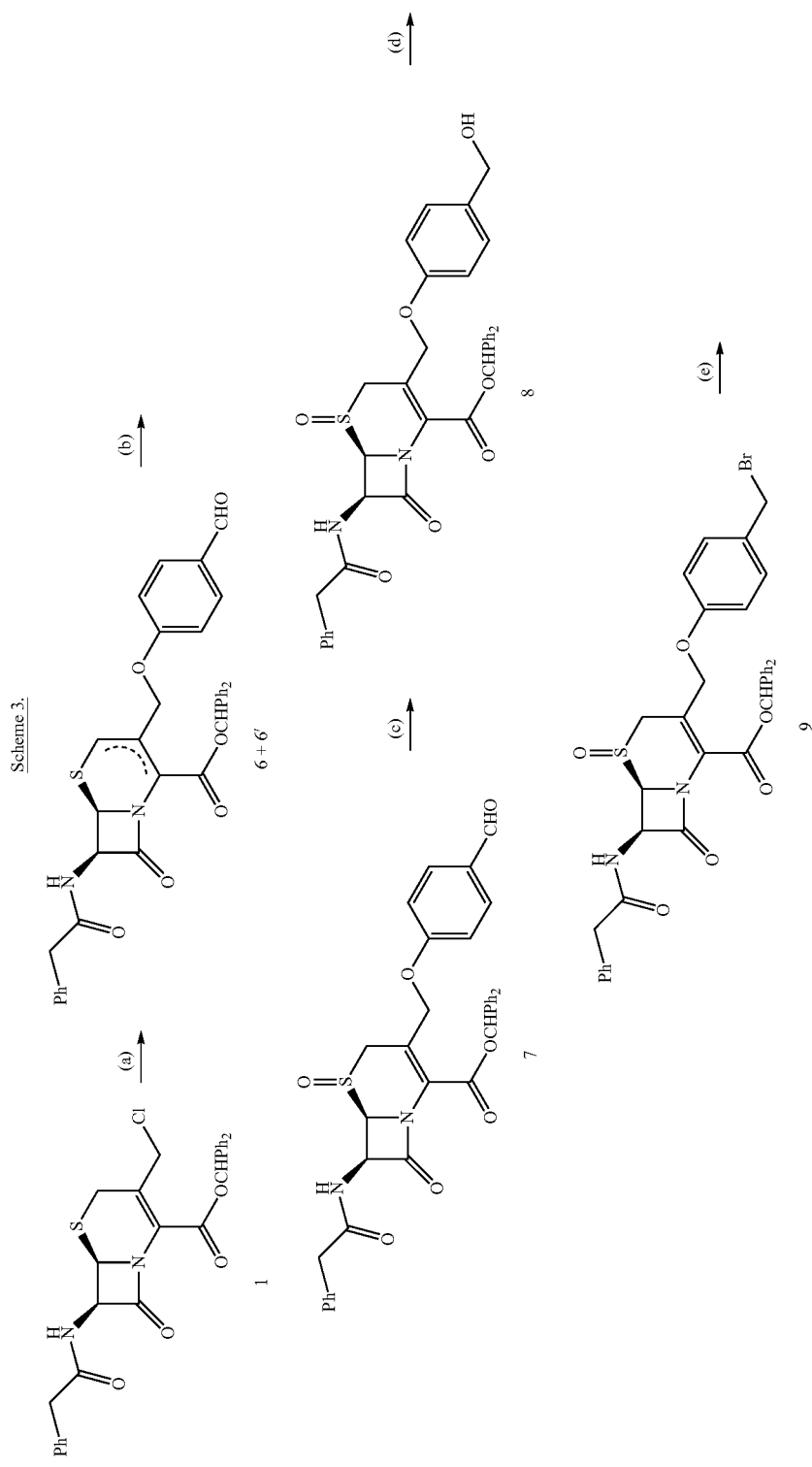

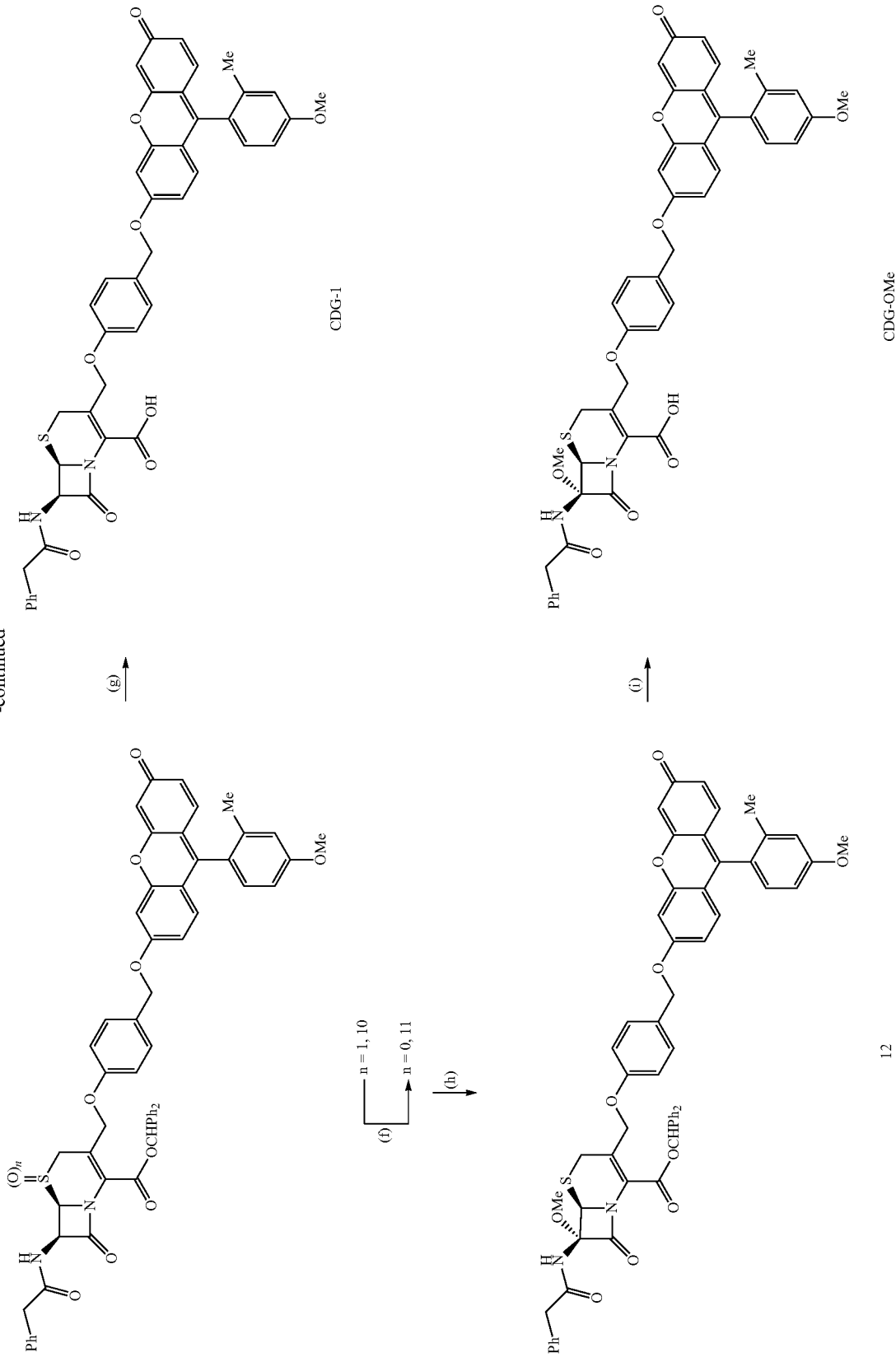

Scheme 3 is a schematic illustration of the preparation of two probes (CDG-1 and CDG-OMe): (a) NaI, 4-hydroxybenzaldehyde, $K_2CO_3$, $CH_3CN$, rt, 3 h; (b) mCPBA, DCM, 0° C., 0.5 h, 54% from 1; (c) $NaBH_4$, DCM/MeOH, rt, 2.5 h; (d) MsCl, TEA, DCM, 0° C., 2 h, then LiBr, DMF, rt, 4 h, 75% from 7; (e) $KHCO_3$, 18-C-6, Tokyo Green, DMF, rt, 4 h; (f) NaI, TFAA, acetone, 0° C., 1 h, 29% from 9; (g) DCM/TFA/TIPS/$H_2O$ (90/5/2.5/2.5), 7 h, rt, 43%; (h) tBuOCl, LiOMe, THF, MeOH, −78° C., 0.5 h, 64%; and (i) DCM/TFA/TIPS/$H_2O$ (90/5/2.5/2.5), 7 h, rt, 37%.

Figure 5B:
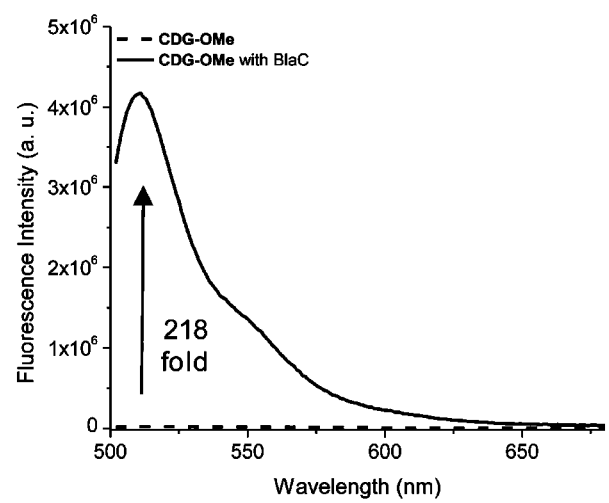
Figure 5C:
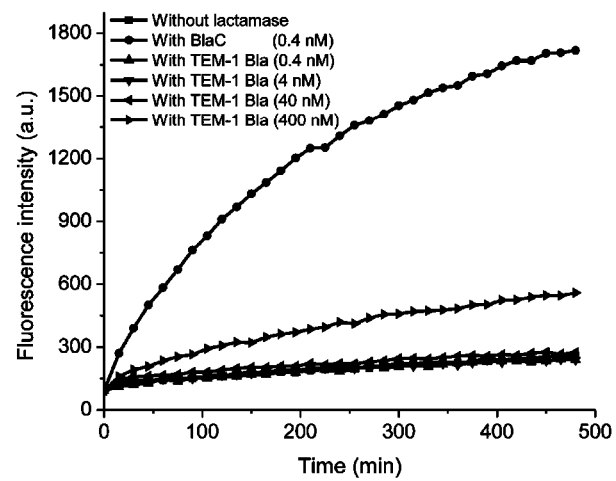
Figure 5D:
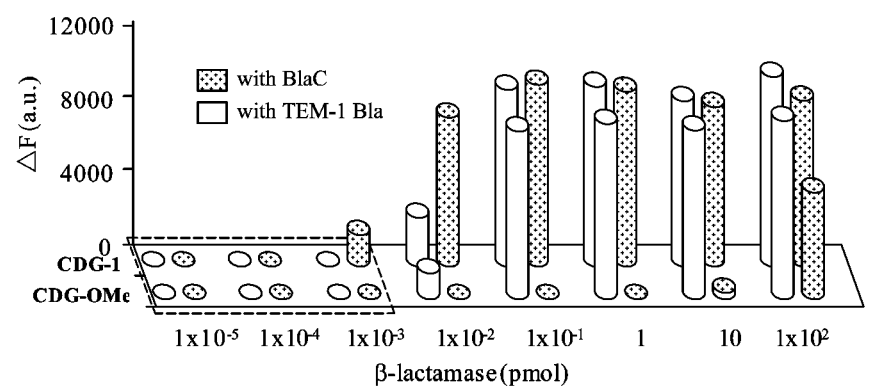
Figure 5E:
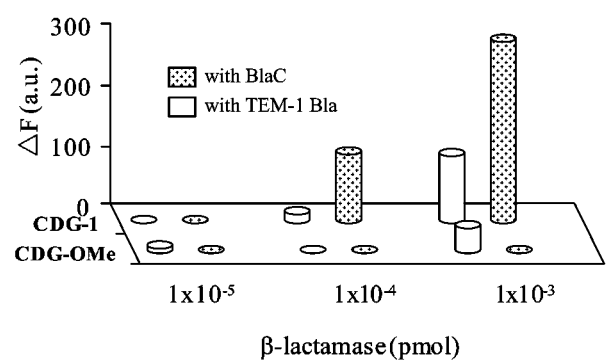

Upon treatment with BlaC, the fluorescence emission of CDG-OMe at 520 nm increases up to 218-fold (FIG. 5B). In addition to the gain in the stability of the probe obtained from the additional linker, the specificity of CDG-OMe for BlaC improves with its $k_{cat}/K_m$ increase by 11-fold to $2.4 \times 10^5$ $s^{-1}M^{-1}$ in PBS (Table 1). Even at a more than 1000-fold higher concentration, the fluorescence signal of CDG-OMe generated by TEM-1 Bla (400 nM) was just 30% of that by BlaC (400 pM) in 300 mins, confirming its high selectivity for BlaC (FIG. 5C). Less than 1 fmol of BlaC was readily detectable with CDG-OMe after 8 hours incubation (FIG. 5D).

Figure 6A:
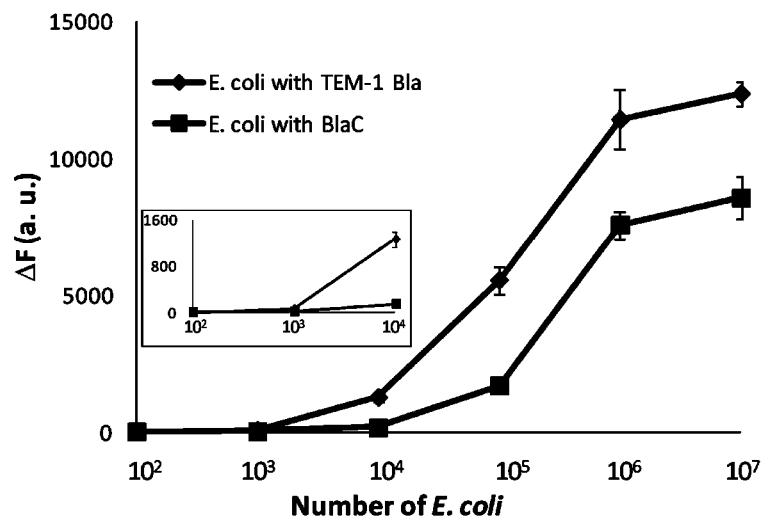
FIGS. 6A-6E illustrate the detection and imaging of live bacteria with fluorescent probes CDG-1 and CDG-OMe.
Figure 6B:
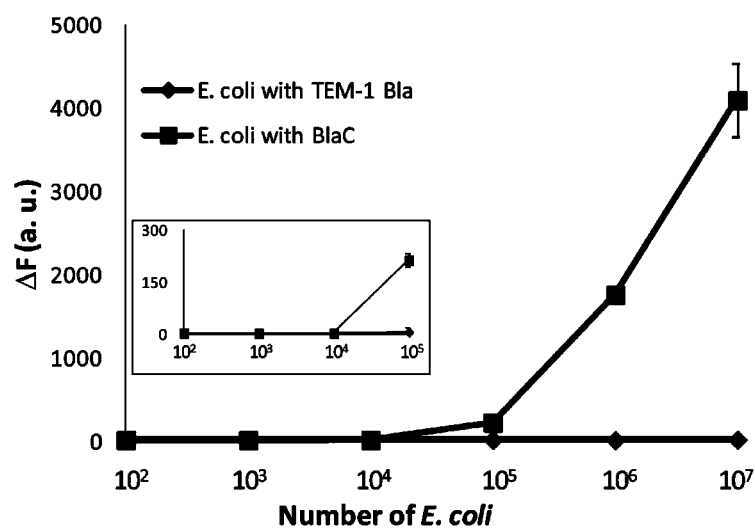
Figure 6C:
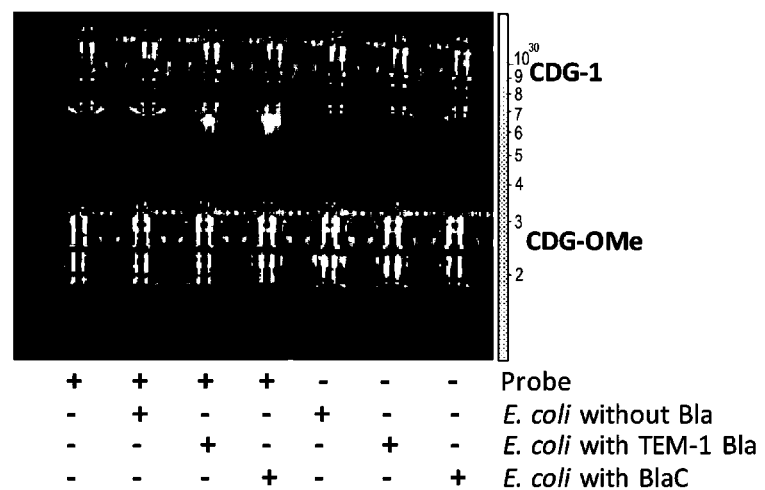
Figure 6D:
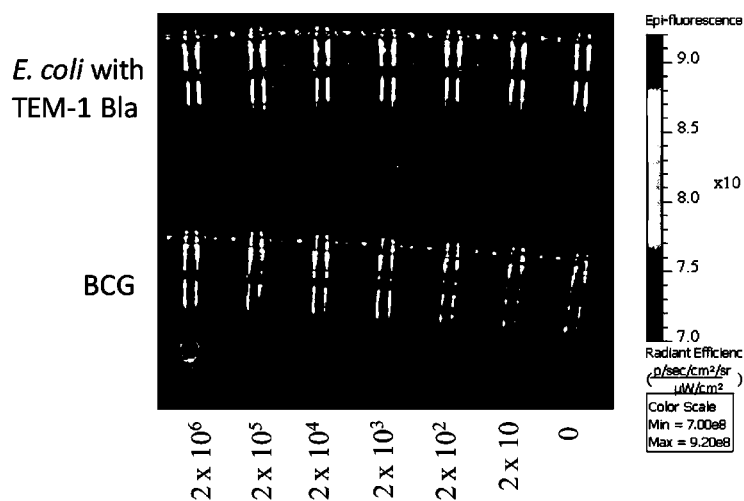
Figure 6E:
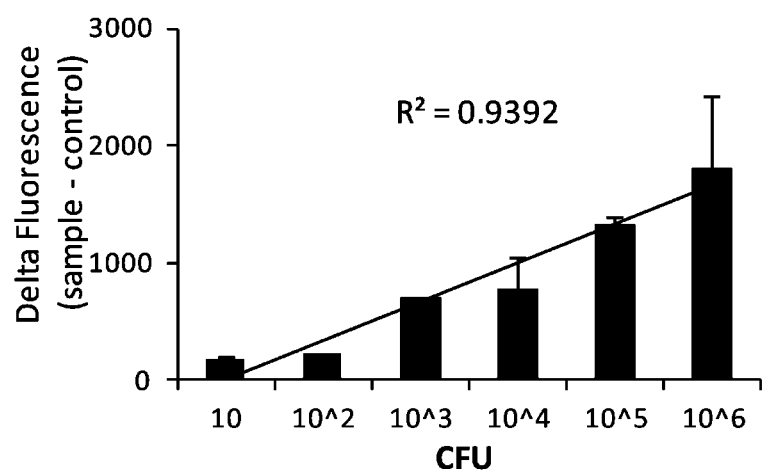

To assess the utility of CDG-OMe for Mtb detection, various numbers of TEM-1 Bla- or BlaC-expressing *E. coli* where first incubated with CDG-1 and CDG-OMe. Consistent with the in vitro results, CDG-1 displayed no selectivity and was able to detect approximately 1,000 TEM-1 Bla-carrying *E. coli* and 10,000 BlaC-carrying *E. coli* with 6 hours incubation (FIG. 6A). In contrast, CDG-OMe showed excellent selectivity for BlaC over TEM-1 Bla in *E. coli* (FIGS. 6B and 6C): there was no detectable signal from TEM-1 Bla-expressing *E. coli* even at $10^7$ CFU with 6 hour incubation. In contrast, $10^5$ BlaC-expressing *E. coli* gave strong fluorescent signal under the same conditions (FIG. 6B). CDG-OMe emits in the green wavelengths (maximum at 520 nm) after BlaC activation, significantly reducing the autofluorescence due to BCG in comparison to CDC-OMe. Fluorescent emission was observed for BCG with just 20 min incubation of CDG-OMe when the bacterial number was $2 \times 10^5$ CFU (FIG. 6D). When the incubation time increased to 438 mins, as low as $10^3$ CFU BCG were detected (FIG. 6E). These results demonstrate that CDG-OMe can detect live *M. tuberculosis* var. *Bovis* strain BCG rapidly and at a high sensitivity and specificity.

The following examples are provided for the purpose of illustrating, not limiting, the invention.

EXAMPLES

Example 1

Materials and Methods

All chemicals were purchased from commercial sources (e.g., Aldrich, Fluka, ANASPEC, and Novabiochem). 7-Amino-3-chloromethyl 3-cephem-4-carboxylic acid diphenylmethyl ester hydrochloride (ACLH) was obtained from Otsuka Chemical Co., Ltd. The purified TEM-1 β-lactamase was customarily prepared by the Biologics Process Development, Inc. (San Diego, Calif.). Analytical TLC was performed with 0.25 mm silica gel 60F plates with fluorescent indicator (254 nm). Plates were visualized by ultraviolet light. $^1H$ and $^{13}C$ NMR spectra were taken on Varian 300 MHz or 400 MHz magnetic resonance spectrometer. Data for $^1H$ NMR spectra are reported as chemical shifts reported as δ in units of parts per million (ppm) relative to chloroform-d (δ 7.26, s); multiplicities are reported as s (singlet), d (doublet), t (triplet), q (quartet), dd (doublet of doublets), m (multiplet), or br (broadened); coupling constants are reported as a J value in Hertz (Hz); the number of protons (n) for a given resonance is indicated nH, and based on the spectral integration values.

Fluorescence spectra were collected on a Fluoromax-3 spectrafluorometer (Jobin Yvon).

Kinetic experiments were conducted in a M1000 microplate reader (TECAN, research triangle park, NC).

HPLC was performed on a Dionex HPLC System (Dionex Corporation) equipped with a GP50 gradient pump and an inline diode array UV-Vis detector. A reversed-phase C18 (Phenomenax, 5 μm, 10×250 mm or Dionex, 5 μm, 4.6×250 mm) column was used with a MeCN/$H_2O$ gradient mobile phase containing 0.1% trifluoroacetic acid at a flow of 1 or 3 mL/min for the analysis.

Cloning, Expression, and Purification of BlaC.

Wild-type BlaC was cloned from *M. tuberculosis* H37Rv genomic DNA as described in Wang, F., Cassidy, C., Sacchettini, J. C. Crystal structure and activity studies of the *Mycobacterium tuberculosis* beta-lactamase reveal its critical role in resistance to beta-lactam antibiotics. Antimicrob. Agents Chemother. 50, 2762-71 (2006)). The deacylation deficient E166A mutant was generated using the QuickchangeTM site directed mutagenesis kit (Stratagene no. 200519). Mutant and wild type protein expression and purification were performed as described in Wang et al. 2006.

Enzymatic Kinetics.

Figure 8C:
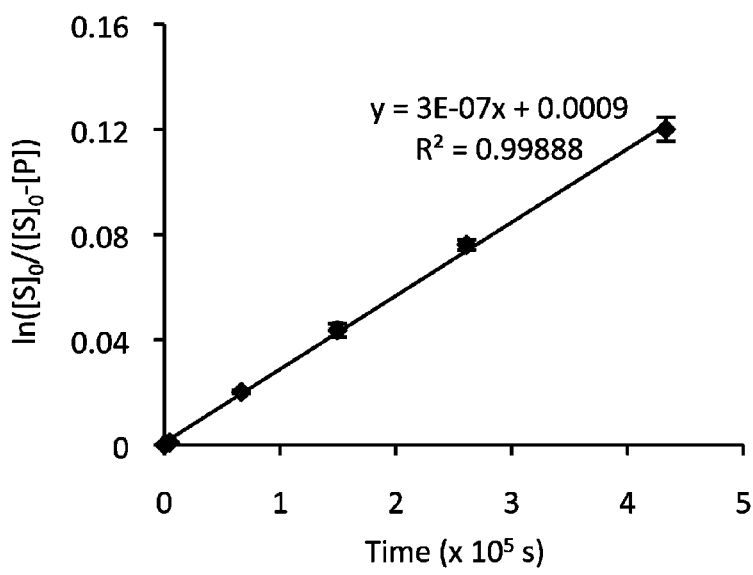
Figure 9:
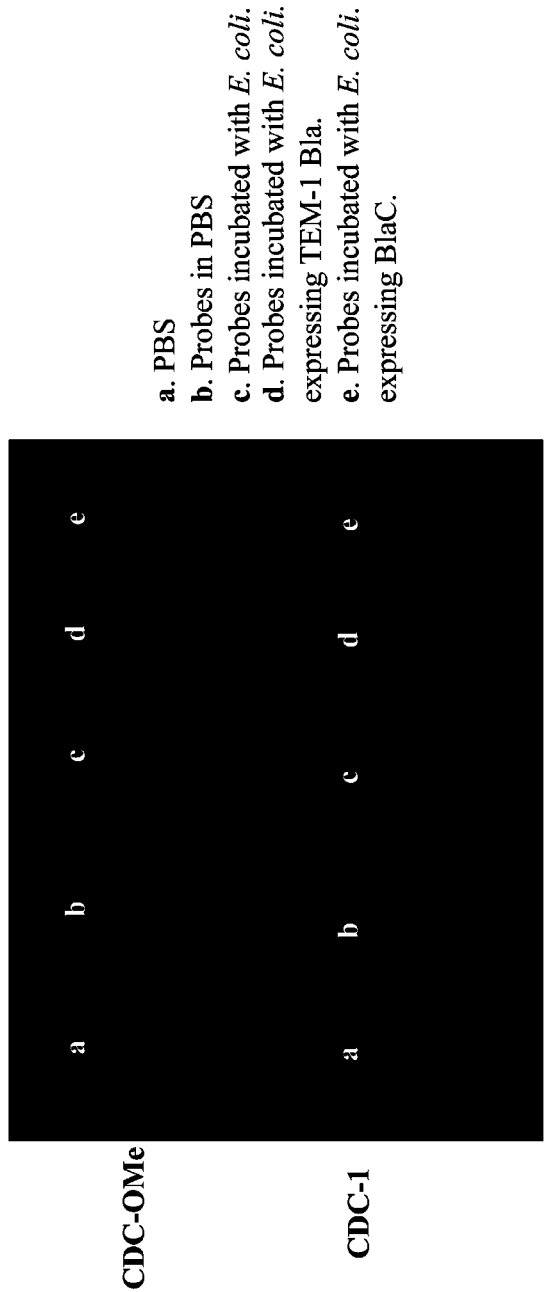
FIG. 9 compares images of E. coli expressing β-lactamases with CDC-OMe and CDC-1 in PBS (1×, pH 7.4).

The following procedure was used for determining the hydrolytic kinetics of the probes by beta-lactamase. To a series of different concentrations of the probe (20, 40, 60, 80, 100, 120, 150 μM) in 1× phosphate-buffered saline (PBS, pH 7.4; 100 μL) in a 96-well plate (black and flat bottom) was added TEM-1 Bla or BlaC in PBS. The fluorescence intensity at 454 nm was immediately measured in a microplate reader (excitation wavelength: 400 nm) over a 20-minute period at 25° C. The values of the kinetic parameters ($K_m$ and $k_{cat}$) were determined from the double-reciprocal plot of the hydrolysis rate versus substrate concentration (Lineweaver-Burk plot). To determine the spontaneous hydrolysis rate of the probes, the fluorescence intensity was monitored over 5 days without the addition of the enzyme. The rate was calculated from the plot of $\ln([S]_0/([S]_0-[P]))$ versus time (FIG. 8C).

Crystallization.

Crystals of wild type and E166A BlaC were grown using the hanging drop vapor diffusion method. BlaC was concentrated to 10 mg/ml and equilibrated overnight at 4° C. with the mother liquor (2.0 M $NH_4H_2PO_4$, 0.1 M Tris pH 8.0) at a 1:1 ratio (protein:mother liquor). The solution was centrifuged for 10 min at 13,000 rpm to remove insoluble precipitate. Hanging drops were set up and equilibrated against 1 ml of mother liquor. Microseeding with horsehair was sufficient to produce large diffraction quality crystals. Crystals were transferred to a stabilization solution containing 30% glycerol in mother liquor and were subsequently soaked with lactam substrates for 2-4 hours. The concentration of substrate was slowly increased by transferring the crystals to successive drops to prevent cracking. Derivatized crystals were flash frozen in liquid nitrogen.

Data Collection and Processing.

X-ray diffraction data was collected on beam lines 19ID and 23ID at the Advanced Photon Source, Argonne National Laboratory, Argonne, Ill. Data sets were reduced using HKL3000. Data was collected at a wavelength of 0.97 Å and a temperature of 120 K.

Structure Determination.

Initial phases were obtained by molecular replacement using Phaser Crystallographic Software in the CCP4 suite and 2GDN as a search model. Each data set was refined against the resulting model, and iterative cycles of model building and refinement were performed with Coot 0.6.1 and PHENIX PDB codes for BlaC-CDC-1 and BlaC-CDC-OMe acyl-intermediate crystal structures are (3VFH) and (3VFF), respectively.

Imaging Mycobacteria.

*Mycobacterium tuberculosis* var. *bovis* strain *bacillus* Calmette Guérin (BCG) was cultured in 7H9 medium with 10% OADC and 0.25% Tween-80 until it reached log phase (optical density at 600 nm ($OD_{600}$) of 0.4-0.6). *E. coli* strain $ec^2420$ (DH5α (Invitrogen) carrying plasmid pBlueScript KSII+ (Stratagene, TEM-1 expressing)) was cultured in Luria Bertani (LB) medium till $OD_{600}$ of 0.4-0.6. Bacteria were washed with MES (define buffer) buffer twice, and resuspended in 1 ml of MES. Based on the $OD_{600}$ of the preparation, a series of bacterial concentrations were made: $1\times10^8$ CFU/ml, $1\times10^7$ CFU/ml, $1\times10^6$ CFU/ml, $1\times10^5$ CFU/ml, $1\times10^4$ CFU/ml, and $1\times10^3$ CFU/ml with MES. 50 μl of each concentration was loaded into 0.2 ml tubes. 50 μl of 16 μM CDG-1 or CDG-OMe were loaded into each tube and mixed with the bacteria immediately before imaging. The negative control was CDG-1 or CDG-OMe in MES without bacteria. Imaging was carried out in an IVIS Spectrum and images were taken every 10 minutes for one hour with excitation at 490 nm and emission at 540 nm.

Example 2

Preparation and Characterization of Representative Coumarin Beta-Lactamase Probes: CDC-1, CDC-2, CDC-3, CDC-4, CDC-5, CDC-OMe and CDC-OEt The following is a description of the preparation and characterization of representative coumarin probes of the invention. The preparations are illustrated schematically in Scheme 2.

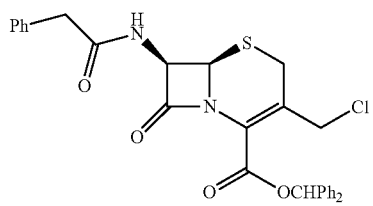

1

(6R,7R)-Benzhydryl 3-(chloromethyl)-8-oxo-7-(2-phenylacetamido)-5-thia-1-aza bicyclo[4.2.0]oct-2-ene-2-carboxylate (1)

Compound 1 was synthesized according to the method reported previously (Gao, W., Xing, B., Tsien, R. Y., Rao, J. Novel fluorogenic substrates for imaging beta-lactamase gene expression. *J. Am. Chem. Soc.* 125, 11146-7 (2003); and Yao, H., So, M. K., Rao, J. A bioluminogenic substrate for in vivo imaging of beta-lactamase activity. *Angew. Chem. Int. Ed.* 46, 7031-7034 (2007)). To a mixture of ACLH (0.85 g, 1.88 mmol), 2,6-lutidine (0.44 mL, 3.80 mmol) in acetonitrile at 0° C. was added phenylacetyl chloride (0.35 mL, 2.6 mmol). The reaction mixture was stirred for 3 minutes at the same temperature before triethylamine (0.25 mL, 1.8 mmol) was added in one port. After overnight stirring with the reaction temperature raised to room temperature, solvent was removed under reduced pressure. The residue was dissolved in ethyl acetate and washed with $NaHCO_3$ (aq.) (30 mL×1) and brine (30 mL×1), subsequently. Drying over $MgSO_4$ followed by flash chromatography purification on a silica gel column afforded the title compound (0.97 g, 97%). $^1$H NMR (400 MHz, $CDCl_3$) δ 7.51-7.16 (m, 15H), 6.95 (s, 1H), 6.36 (d, J=9.1 Hz, 1H), 5.86 (dd, J=9.0, 4.9 Hz, 1H), 4.94 (d, J=4.9 Hz, 1H), 4.38 (d, J=11.9 Hz, 1H), 4.34 (d, J=11.9 Hz, 1H), 3.65 (d, J=15.9 Hz, 1H), 3.59 (d, J=16.1 Hz, 1H), 3.54 (d, J=18.4 Hz, 1H), 3.40 (d, J=18.3 Hz, 1H); $^{13}$C NMR (101 MHz, $CDCl_3$) δ 171.52, 165.07, 160.67, 139.27, 139.13, 133.89, 129.70, 129.41, 128.86, 128.75, 128.57, 128.41, 127.96, 127.94, 127.33, 127.17, 125.79, 80.12, 59.35, 57.93, 43.50, 43.34, 27.36.

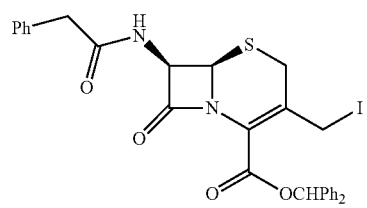

2

(6R,7R)-Benzhydryl 3-(iodomethyl)-8-oxo-7-(2-phenylacetamido)-5-thia-1-aza bicyclo[4.2.0]oct-2-ene-2-carboxylate (2)

Compound 2 was synthesized according to a method previously reported (Gao, W., Xing, B., Tsien, R. Y., Rao, J. Novel fluorogenic substrates for imaging beta-lactamase gene expression. *J. Am. Chem. Soc.* 125, 11146-7 (2003); and Yao, H., So, M. K., Rao, J. A bioluminogenic substrate for in vivo imaging of beta-lactamase activity. *Angew. Chem. Int. Ed.* 46, 7031-7034 (2007)). Under the argon atmosphere, to a solution of 1 (507 mg, 0.95 mmol) in acetone (6 mL) was added sodium iodide (1.43 g, 9.5 mmol). The resulting mixture was stirred at room temperature for one hour and then the solvent was removed under reduced pressure. Water (10 mL) was added and extracted with ethyl acetate (15 mL×3). The combined organic layers were washed with $Na_2S_2O_3$ aqueous solution (20 mL×2) and brine, dried over $MgSO_4$. Title compound 2 was obtained as a crude product after the solvent was removed.

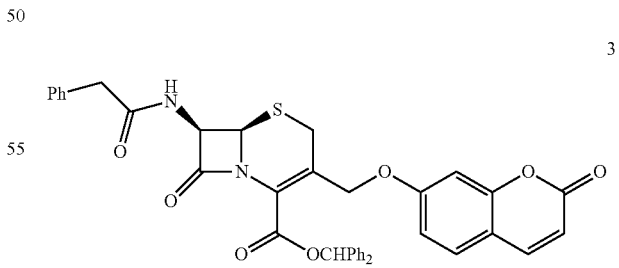

3

(6R,7R)-Benzhydryl 8-oxo-3-((2-oxo-2H-chromen-7-yloxy)methyl)-7-(2-phenylacetamido)-5-thia-1-azabicyclo[4.2.0]oct-2-ene-2-carboxylate (3)

A mixture of 2 (553 mg, 0.88 mmol), $K_2CO_3$ (366 mg, 2.65 mmol) and 7-hydroxycoumarin (287 mg, 1.77 mmol) in acetonitrile (10 mL) was stirred at room temperature for 2.5 hours. Solvent was removed under reduced pressure and the residue was dissolved in water (10 mL) and ethyl acetate (10 mL). The organic layer was separated and the aqueous layer was extracted with ethyl acetate (15 mL×2). The combined organic layers were washed with $Na_2S_2O_3$ aqueous solution (20 mL×2) and brine, dried over $MgSO_4$. Flash chromatography on a short silica gel column was used to remove inorganic impurities and most of the excess 7-hydroxycoumarin. The resulting mixture of 3 and 3', along with small amount of were dissolved in $CH_2Cl_2$ (50 mL) and 3-chloroperoxybenzoic acid (mCPBA, 68%, 159 mg, 0.63 mmol) was added in several ports at 0° C. After stirred at 0° C. for 30 min (monitored with TLC), the reaction mixture was diluted with $CH_2Cl_2$ and washed with $Na_2S_2O_3$ (aq.) (50 mL×1), $NaHCO_3$ (aq.) (50 mL×1) and brine (50 mL×1) subsequently. Drying over $MgSO_4$ followed by purification with flash chromatography on a short silica gel column afforded compound 4 as a crude product. The reduction of compound 4 was performed according to the method reported in Albrecht, H. A. et al. Cephalosporin 3'-Quinolone Esters with a Dual Mode of Action. *J. Med. Chem.* 33, 77-86 (1990). Under argon atmosphere, to a mixture of 4 (304 mg, 0.45 mmol) and NaI (339 mg, 2.25 mmol) in anhydrous acetone (10 mL) at 0° C. was added dropwise trifluoroacetic anhydride (TFAA) (344 μL, 2.5 mmol). The resulting mixture was stirred at 0° C. for one hour and then the solvent and volatile reagent was removed under reduced pressure. The residue was dissolved in $NaHCO_3$ (aq.) (10 mL) and extracted with ethyl acetate (10 mL×3). After purification with flash chromatography on a silica gel column, the title compound 3 was obtained as solid at an overall yield of 45% from 1. $^1$H NMR (400 MHz, $CDCl_3$) δ 7.61 (d, J=9.5 Hz, 1H), 7.43-7.20 (m, 15H), 6.93 (s, 1H), 6.71 (dd, J=8.6, 2.5 Hz, 1H), 6.64 (d, J=2.4 Hz, 1H), 6.27 (d, J=9.5 Hz, 1H), 6.26 (d, J=9.1 Hz, 1H), 5.89 (dd, J=9.1, 4.9 Hz, 1H), 4.97 (d, J=4.9 Hz, 1H), 4.93 (d, J=13.1 Hz, 1H), 4.81 (d, J=13.1 Hz, 1H), 3.67 (d, J=16.0 Hz, 1H), 3.62 (d, J=16.0 Hz, 1H), 3.58 (d, J=18.7 Hz, 1H), 3.50 (d, J=18.7 Hz, 1H); $^{13}$C NMR (101 MHz, $CDCl_3$) δ 171.44, 165.20, 161.15, 161.11, 161.02, 155.88, 143.43, 139.24, 139.11, 133.84, 129.73, 129.44, 129.19, 128.88, 128.77, 128.58, 128.44, 127.99, 127.81, 127.19, 125.30, 113.94, 113.38, 112.59, 102.07, 80.11, 67.40, 59.37, 57.70, 43.55, 26.27.

J=9.6 Hz, 1H), 7.66 (d, J=8.6 Hz, 1H), 7.41-7.18 (m, 4H), 7.05 (d, J=2.3 Hz, 1H), 7.00 (dd, J=8.6, 2.4 Hz, 1H), 6.32 (d, J=9.5 Hz, 1H), 5.72 (dd, J=8.3, 4.7 Hz, 1H), 5.14 (d, J=4.8 Hz, 1H), 5.01 (d, J=12.0 Hz, 1H), 4.92 (d, J=12.0 Hz, 1H), 3.71 (d, J=18.3 Hz, 1H), 3.62 (d, J=18.3 Hz, 1H), 3.57 (d, J=13.9 Hz, 1H), 3.50 (d, J=13.9 Hz, 1H); $^{13}$C NMR (75 MHz, $d_6$-DMSO) δ 171.90, 165.83, 163.90, 162.12, 161.18, 156.21, 145.24, 136.74, 130.55, 129.96, 129.19, 127.45, 124.40, 113.76, 113.69, 102.44, 68.09, 60.10, 58.47, 42.54, 26.48; HRMS: Calculated for $C_{25}H_{20}N_2NaO_7S^+$ ([M+Na]$^+$): 515.0889. Found: 515.0887.

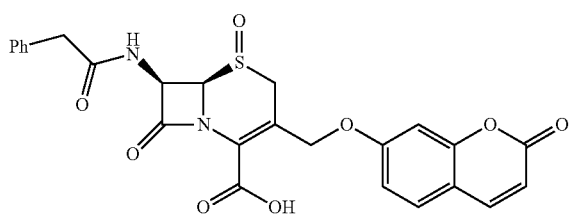

CDC-2

(5S,6R,7R)-8-Oxo-3-(((2-oxo-2H-chromen-7-yl)oxy)methyl)-7-(2-phenylacetamido)-5-thia-1-azabicyclo[4.2.0]oct-2-ene-2-carboxylic acid 5-oxide (CDC-2)

The title compound was obtained from the deprotection of compound 4 as described above. $^1$H NMR (400 MHz, $d_6$-DMSO) δ 8.44 (d, J=8.3 Hz, 1H), 7.98 (d, J=9.5 Hz, 1H), 7.63 (d, J=8.6 Hz, 1H), 7.32-7.25 (m, 4H), 7.25-7.18 (m, 1H), 6.97 (d, J=2.4 Hz, 1H), 6.94 (dd, J=8.6, 2.4 Hz, 1H), 6.29 (d, J=9.5 Hz, 1H), 5.80 (dd, J=8.2, 4.7 Hz, 1H), 5.12 (d, J=12.4 Hz, 1H), 4.96-4.82 (m, 2H), 3.97 (d, J=18.5 Hz, 1H), 3.68 (d, J=14.0 Hz, 1H), 3.61 (d, J=18.7 Hz, 1H), 3.53 (d, J=14.0 Hz, 1H); $^{13}$C NMR (101 MHz, DMSO) δ 171.73, 164.90, 162.89, 161.71, 160.89, 155.92, 144.94, 136.50, 130.30, 129.77, 128.96, 127.22, 113.51, 102.23, 68.17, 66.99, 58.92, 45.94, 42.13; HRMS: Calculated for $C_{25}H_{21}N_2O_8S^+$ ([M+H]$^+$): 509.1013. Found: 509.1006.

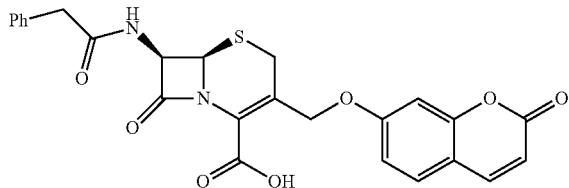

CDC-1

(6R,7R)-8-Oxo-3-((2-oxo-2H-chromen-7-yloxy)methyl)-7-(2-phenylacetamido)-5-thia-1-azabicyclo[4.2.0]oct-2-ene-2-carboxylic acid (CDC-1)

To a solution of $CH_2Cl_2$:TFA:TIPS:$H_2O$=50:45:2.5:2.5 (4 mL) was added compound 3 (65 mg, 0.1 mmol) and the mixture was stirred at room temperature for 10 min (monitored with HPLC). RP-HPLC purification on a C18 column afforded the title compound CDC-1 (39 mg, 80%). $^1$H NMR (300 MHz, $d_6$-DMSO) δ 9.16 (d, J=8.3 Hz, 1H), 8.02 (d,

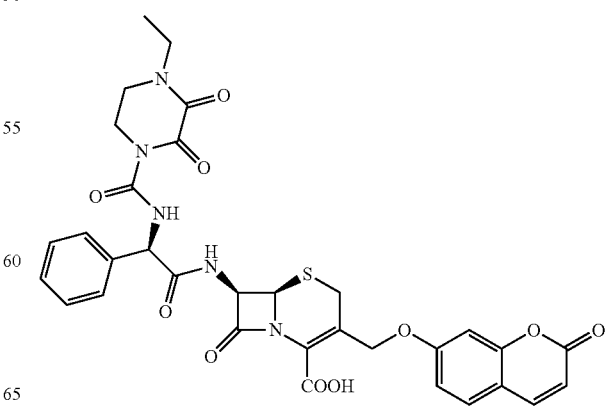

CDC-3

(6R,7R)-7-((R)-2-(4-Ethyl-2,3-dioxopiperazine-1-carboxamido)-2-phenylacetamido)-8-oxo-3-((2-oxo-2H-chromen-7-yloxy)methyl)-5-thia-1-azabicyclo[4.2.0]oct-2-ene-2-carboxylic acid (CDC-3)

The title compound was prepared with the same method as that of CDC-1. $^1$H NMR (300 MHz, d$_6$-DMSO) δ 9.87 (d, J=7.3 Hz, 1H), 9.52 (d, J=8.4 Hz, 1H), 8.01 (d, J=9.5 Hz, 1H), 7.65 (d, J=8.6 Hz, 1H), 7.55-7.26 (m, 5H), 7.03 (d, J=2.2 Hz, 1H), 6.98 (dd, J=8.6, 2.3 Hz, 1H), 6.32 (d, J=9.5 Hz, 1H), 5.79 (dd, J=8.4, 4.9 Hz, 1H), 5.64 (d, J=7.3 Hz, 1H), 5.08 (d, J=4.9 Hz, 1H), 4.98 (d, J=12.0 Hz, 1H), 4.89 (d, J=12.1 Hz, 1H), 3.95-3.88 (m, 2H), 3.64-3.48 (m, 4H), 3.43-3.39 (m, 2H), 1.09 (t, J=7.1 Hz, 3H); $^{13}$C NMR (75 MHz, d$_6$-DMSO) δ 170.95, 165.27, 163.84, 162.11, 161.18, 160.49, 156.32, 156.20, 152.90, 145.24, 138.82, 130.54, 129.48, 128.97, 127.57, 113.74, 113.68, 102.43, 68.05, 59.62, 58.40, 57.79, 43.74, 42.60, 26.42, 12.89. HRMS: Calculated for C$_{32}$H$_{29}$N$_5$NaO$_{10}$S$^+$ ([M+Na]$^+$): 698.1533. Found: 698.1533.

CDC-4

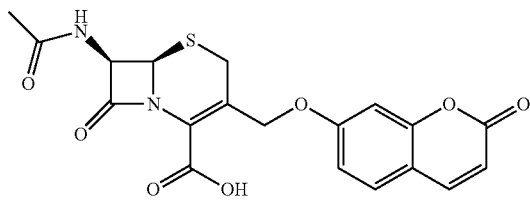

(6R,7R)-7-Acetamido-8-oxo-3-(((2-oxo-2H-chromen-7-yl)oxy)methyl)-5-thia-1-azabicyclo[4.2.0]oct-2-ene-2-carboxylic acid (CDC-4)

The title compound was prepared with the same method as that of CDC-1. $^1$H NMR (400 MHz, DMSO) δ 8.85 (d, J=8.4 Hz, 1H), 7.98 (d, J=9.5 Hz, 1H), 7.62 (d, J=8.6 Hz, 1H), 7.01 (d, J=2.2 Hz, 1H), 6.96 (dd, J=8.6, 2.3 Hz, 1H), 6.29 (d, J=9.5 Hz, 1H), 5.69 (dd, J=8.4, 4.8 Hz, 1H), 5.11 (d, J=4.8 Hz, 1H), 4.98 (d, J=12.0 Hz, 1H), 4.90 (d, J=12.0 Hz, 1H), 3.68 (d, J=18.2 Hz, 1H), 3.57 (d, J=18.2 Hz, 1H), 1.89 (s, 3H); $^{13}$C NMR (101 MHz, DMSO) δ 170.70, 165.76, 163.67, 161.85, 160.90, 155.93, 144.95, 130.27, 127.37, 123.99, 113.48, 113.41, 102.17, 67.84, 59.75, 58.12, 26.21, 22.73; HRMS: Calculated for C$_{19}$H$_{17}$N$_2$O$_7$S$^+$ ([M+H]$^+$): 417.0751. Found: 417.0748.

5

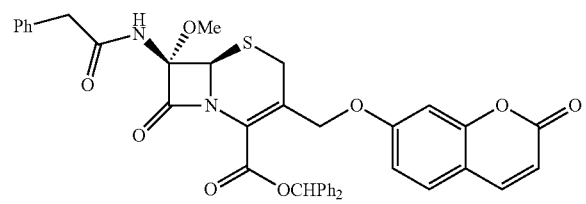

(6R,7S)-Benzhydryl 7-methoxy-8-oxo-3-((2-oxo-2H-chromen-7-yloxy)methyl)-7-(2-phenylacetamido)-5-thia-1-azabicyclo[4.2.0]oct-2-ene-2-carboxylate (5)

Title compound 5 was synthesized according to the method reported in Koppel, G. A., Koehler, R. E. Functionalization of C$_{6(7)}$ of penicillins and cephalosporins. A one-step stereoselective synthesis of 7-α-methoxycephalosporin C. *J. Am. Chem. Soc.* 95, 2403-2404 (1973). Under the argon atmosphere, to a solution of lithium methoxide (13 mg, 0.34 mmol) in anhydrous THF (4 mL) and anhydrous methanol (0.64 mL) at −78° C. was added dropwise a solution of compound 3 (105 mg, 0.16 mmol) in anhydrous THF (1.4 mL). Tert-butyl hypochlorite (29 µL, 0.26 mmol) was then added dropwise and the mixture was stirred at the same temperature for half hour. The reaction solution was poured in one port to an ammonium chloride aqueous solution and extracted with ethyl acetate (15 mL×3). Subsequent purification with flash chromatography on a silica gel column afforded the title compound 5 (80 mg, 73%). $^1$H NMR (400 MHz, CDCl$_3$) δ 7.63 (d, J=9.5 Hz, 1H), 7.46-7.20 (m, 16H), 7.06 (s, 1H), 6.93 (s, 1H), 6.73 (dd, J=8.6, 2.4 Hz, 1H), 6.67 (d, J=2.2 Hz, 1H), 6.39 (s, 1H), 6.28 (d, J=9.5 Hz, 1H), 5.07 (s, 1H), 4.94 (d, J=13.2 Hz, 1H), 4.89 (d, J=13.2 Hz, 1H), 3.69 (s, 2H), 3.56 (d, J=17.8 Hz, 1H), 3.46 (s, 3H), 3.40 (d, J=17.8 Hz, 1H); $^{13}$C NMR (101 MHz, CDCl$_3$) δ 171.96, 161.30, 161.19, 160.97, 160.62, 155.88, 143.45, 139.38, 139.28, 133.98, 132.85, 129.56, 129.53, 129.18, 128.84, 128.77, 128.54, 128.44, 128.09, 127.58, 127.13, 125.64, 113.94, 113.40, 112.69, 102.12, 95.89, 79.94, 77.60, 77.28, 76.96, 66.80, 64.84, 53.86, 44.03, 26.69.

CDC-OMe

(6R,7S)-7-Methoxy-8-oxo-3-((2-oxo-2H-chromen-7-yloxy)methyl)-7-(2-phenylacetamido)-5-thia-1-azabicyclo[4.2.0]oct-2-ene-2-carboxylic acid (CDC-OMe)

To a solution of CH$_2$Cl$_2$:TFA:TIPS:H$_2$O=50:45:2.5:2.5 (2 mL) was added compound 5 (80 mg, 0.12 mmol) and the mixture was stirred at room temperature for 5 min (monitored with HPLC). RP-HPLC purification on a C18 column afforded the title compound CDC-OMe (50 mg, 84%). $^1$H NMR (300 MHz, d$_6$-DMSO) δ 9.48 (s, 1H), 8.01 (d, J=9.5 Hz, 1H), 7.65 (d, J=8.6 Hz, 1H), 7.42-7.17 (m, 5H), 7.05 (d, J=2.3 Hz, 1H), 6.98 (dd, J=8.6, 2.4 Hz, 1H), 6.32 (d, J=9.5 Hz, 1H), 5.18 (s, 1H), 4.96 (d, J=11.9 Hz, 1H), 4.85 (d, J=12.2 Hz, 1H), 3.69-3.40 (m, 4H), 3.36 (s, 3H); $^{13}$C NMR (75 MHz, d$_6$-DMSO) δ 172.48, 163.61, 162.09, 161.37, 161.18, 156.20, 145.23, 136.53, 130.52, 130.09, 129.17, 127.46, 113.74, 113.68, 102.43, 96.07, 67.98, 63.72, 53.43, 42.63, 26.72; HRMS: Calculated for C$_{26}$H$_{22}$N$_2$NaO$_8$S$^+$ ([M+Na]$^+$): 545.0995. Found: 545.0990.

CDC-OEt

(6R,7S)-7-Ethoxy-8-oxo-3-((2-oxo-2H-chromen-7-yloxy)methyl)-7-(2-phenylacetamido)-5-thia-1-azabicyclo[4.2.0]oct-2-ene-2-carboxylic acid (CDC-OEt)

The title compound was prepared with the same method as that of CDC-OMe. $^1$H NMR (400 MHz, CD$_3$CN) δ 7.81 (d, J=9.5 Hz, 1H), 7.60-7.47 (m, 2H), 7.33 (qd, J=8.4, 5.1 Hz, 5H), 6.94-6.90 (m, 2H), 6.24 (d, J=9.6 Hz, 1H), 5.04 (s, 1H), 5.00 (d, J=12.4 Hz, 1H), 4.91 (d, J=12.4 Hz, 1H), 3.80-3.70 (m, 2H), 3.63-3.53 (m, 3H), 3.43 (d, J=18.2 Hz, 1H), 1.17 (t, J=7.0 Hz, 3H); $^{13}$C NMR (75 MHz, d$_6$-DMSO) δ 172.36, 163.66, 162.10, 161.19, 156.21, 145.24, 136.55, 130.53, 130.09, 129.15, 127.44, 113.75, 113.68, 102.43, 95.64, 68.02, 64.03, 61.57, 42.66, 26.72, 16.08. HRMS: Calculated for C$_{27}$H$_{24}$N$_2$NaO$_8$S$^+$ ([M+Na]$^+$): 559.1151. Found: 559.1146.

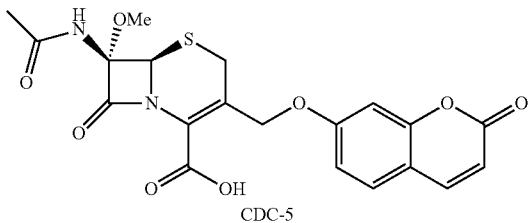

CDC-5

(6R,7S)-7-Acetamido-7-methoxy-8-oxo-3-(((2-oxo-2H-chromen-7-yl)oxy)methyl)-5-thia-1-azabicyclo[4.2.0]oct-2-ene-2-carboxylic acid (CDC-5)

The title compound was prepared with same method as that of CDC-OMe. $^1$H NMR (400 MHz, DMSO) δ 9.20 (s, 1H), 7.97 (d, J=9.6 Hz, 1H), 7.62 (d, J=8.6 Hz, 1H), 7.01 (d, J=2.4 Hz, 1H), 6.95 (dd, J=8.6, 2.2 Hz, 1H), 6.28 (d, J=9.5 Hz, 1H), 5.16 (s, 1H), 4.93 (d, J=12.0 Hz, 1H), 4.84 (d, J=12.0 Hz, 1H), 3.65 (d, J=18.2 Hz, 1H), 3.43 (d, J=18.2 Hz, 1H), 3.37 (s, 3H), 1.93 (s, 3H); $^{13}$C NMR (101 MHz, DMSO) δ 171.46, 163.35, 161.80, 161.27, 160.91, 155.93, 144.93, 130.26, 127.25, 124.57, 113.46, 113.43, 102.13, 95.85, 67.66, 63.45, 53.18, 26.44, 23.08. HRMS: Calculated for C$_{20}$H$_{19}$N$_2$O$_8$S$^+$ ([M+H]$^+$): 447.0857. Found: 447.0849.

Example 3

Preparation and Characterization of Representative TOKYO GREEN® Beta-Lactamase Probes: CDG-1 and CDG-OMe The following is a description of the preparation and characterization of representative TOKYO GREEN® probes of the invention. The preparations are illustrated schematically in Scheme 3.

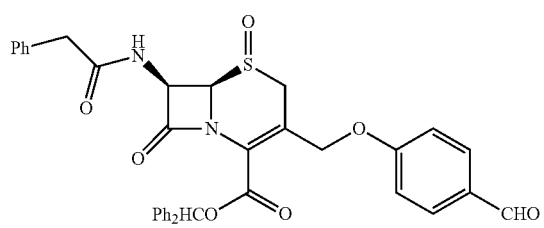

7

(5S,6R,7R)-Benzhydryl 3-((4-formylphenoxy)methyl)-8-oxo-7-(2-phenylacetamido)-5-thia-1-azabicyclo[4.2.0]oct-2-ene-2-carboxylate 5-oxide (7)

A mixture of 1 (2.00 g, 3.76 mmol), K$_2$CO$_3$ (1.04 g, 7.54 mmol), sodium iodide (564 mg, 3.76 mmol) and 4-hydroxybenzaldehyde (1.38 g, 11.3 mmol) in acetonitrile (70 mL) was stirred at room temperature until starting material 1 disappeared (monitored by TLC). Solvent was removed under reduced pressure and the residue was dissolved in water (20 mL) and ethyl acetate (60 mL) again. The organic layer was separated and the aqueous layer was extracted with ethyl acetate (60 mL×2). The combined organic layers were washed with Na$_2$S$_2$O$_3$ aqueous solution and brine, dried over MgSO$_4$. Compound 6 and its isomer 6' were obtained as mixture after purification by flash chromatography on silica gel column, which were then oxidized with mCPBA as described above to afford 1.28 g of the title compound 7 (yield: 54% from compound 1). $^1$H NMR (400 MHz, CDCl$_3$) δ 9.87 (s, 1H), 7.76 (d, J=8.8 Hz, 2H), 7.47-7.44 (m, 2H), 7.42-7.22 (m, 13H), 6.95 (s, 1H), 6.84-6.78 (m, 3H), 6.11 (dd, J=9.9, 4.8 Hz, 1H), 5.28 (d, J=13.9 Hz, 1H), 4.76 (d, J=13.9 Hz, 1H), 4.47 (dd, J=4.8, 1.5 Hz, 1H), 3.97 (d, J=19.0 Hz, 1H), 3.66 (d, J=15.6 Hz, 1H), 3.61 (d, J=15.6 Hz, 1H), 3.26 (d, J=19.0 Hz, 1H); $^{13}$C NMR (101 MHz, CDCl$_3$) δ 190.87, 171.58, 164.48, 162.61, 160.14, 139.09, 139.07, 133.83, 132.28, 130.89, 129.61, 129.29, 128.95, 128.85, 128.58, 127.86, 127.68, 127.26, 124.82, 122.61, 114.98, 80.72, 67.52, 67.06, 59.28, 45.57, 43.58; HRMS: Calculated for C$_{36}$H$_{30}$N$_2$NaO$_7$S$^+$ ([M+Na]$^+$): 657.1666. Found: 657.1659.

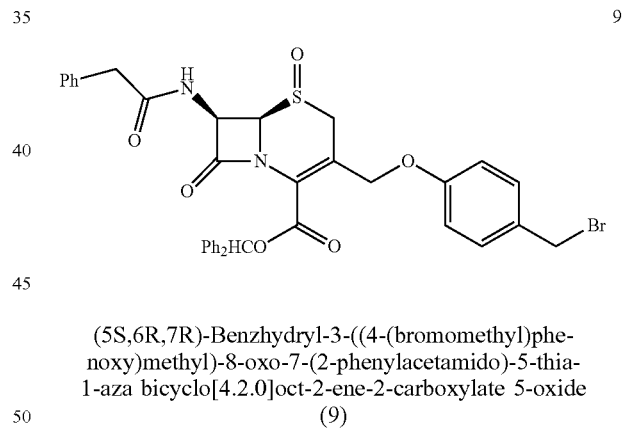

9

(5S,6R,7R)-Benzhydryl-3-((4-(bromomethyl)phenoxy)methyl)-8-oxo-7-(2-phenylacetamido)-5-thia-1-aza bicyclo[4.2.0]oct-2-ene-2-carboxylate 5-oxide (9)

To a solution of 7 (1.214 g, 1.91 mmol) in DCM (60 mL) and MeOH (60 mL) at 0° C. was added sodium borohydride (80 mg, 2.1 mmol) in several portions. The resulting mixture was stirred at the same temperature until the disappearance of the starting material indicated by TLC (about 0.5 hour). Water and 1 N HCl were then added to neutralize the reaction mixture, organic lay was separated and aqueous lay was extracted with DCM (40 mL×3). The combined organic layers were dried over MgSO$_4$ and solvent was removed via Rota-Vap to afford 8 as crude product. To a solution of crude 8 (prepared above), TEA (0.42 mL, 3.0 mmol) in DCM (100 mL) and DMF (10 mL) at 0° C. was added dropwise methanesulfonyl chloride (0.21 mL, 2.8 mmol) and the resulting mixture was stirred for additional two hours before washed with water and dried over MgSO$_4$. After solvent was removed via Rota-Vap, the residue was re-dissolved in DMF and lithium bromide (3.2 g, 36.8 mmol) was added slowly. After stirred for 3 hours at room temperature, DCM was added and washed with water. Purification with flash chromatography on silica gel column recovered starting material 8 (478 mg) and afforded the title compound 9 (610 mg, 75% calculated from the consumed starting material 7). $^1$H NMR (400 MHz, CDCl$_3$) δ 7.46 (d, J=7.1 Hz, 2H), 7.43-7.19 (m, 15H), 6.95 (s, 1H), 6.81 (d, J=9.9 Hz, 1H), 6.69 (d, J=8.7 Hz, 2H), 6.09 (dd, J=9.9, 4.6 Hz, 1H), 5.23 (d, J=14.2 Hz, 1H), 4.68 (d, J=14.2 Hz, 1H), 4.53 (s, 2H), 4.43 (d, J=4.2 Hz, 1H), 3.97 (d, J=19.2 Hz, 1H), 3.65 (d, J=15.6 Hz, 1H), 3.60 (d, J=15.7 Hz, 1H), 3.23 (d, J=19.1 Hz, 1H); $^{13}$C NMR (101 MHz, CDCl$_3$) δ 171.57, 164.50, 160.16, 157.81, 144.07, 139.20, 139.14, 133.87, 130.47, 129.62, 129.28, 128.94, 128.83, 128.53, 127.84, 127.68, 127.29, 126.77, 124.39, 123.79, 114.88, 80.60, 67.30, 66.99, 59.21, 46.18, 45.58, 43.59; HRMS: Calculated for $C_{36}H_{31}BrN_2NaO_6S^+$ ([M+Na]$^+$): 721.0978. Found: 721.0968.

Kamiya, M., Kanda, K., Ueno, T., Hirose, K., Nagano, T. Evolution of fluorescein as a platform for finely tunable fluorescence probes. J. Am. Chem. Soc. 127, 4888-4894 (2005), KHCO$_3$ (193 mg, 1.93 mmol)) and 18-crown-6 (204 mg, 0.77 mmol) in DMF (anhydrous, 3 mL) was stirred at room temperature for 10 min. Compound 9 was then added to the above mixture and stirred at room temperature for 4 h (monitored by HPLC). DCM was added and washed with water. Flash chromatography purification on silica gel column afforded 269 mg of compound 10, which contained a small amount of impurities and was used in the next step without further purification. The reduction of compound 10 to the titled compound was performed as previous described. $^1$H NMR (400 MHz, CDCl$_3$) δ 7.42-7.24 (m, 17H), 7.07 (d,

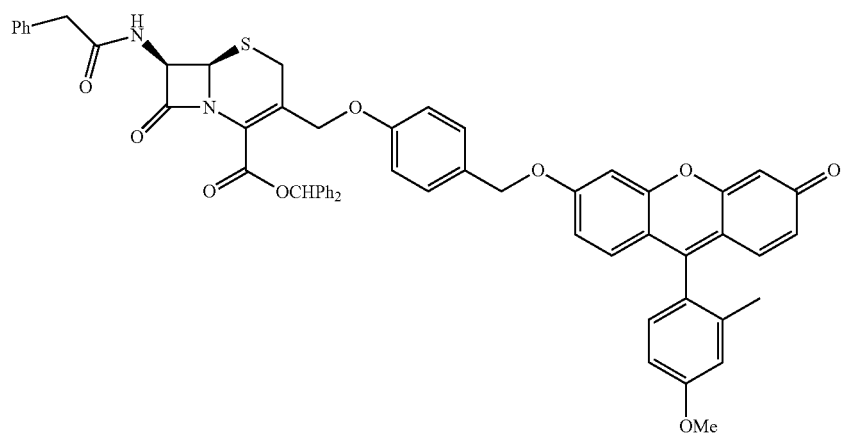

11

(6R,7R)-Benzhydryl 3-((4-(((9-(4-methoxy-2-methylphenyl)-3-oxo-3H-xanthen-6-yl)oxy)methyl) phenoxy)methyl)-8-oxo-7-(2-phenylacetamido)-5-thia-1-azabicyclo[4.2.0]oct-2-ene-2-carboxylate (11)

A mixture of TOKYO GREEN® (321 mg, 0.97 mmol, prepared using the procedures described in Urano, Y., J=8.8 Hz, 2H), 7.04-7.02 (m, 2H), 6.93 (s, 2H), 6.90-6.82 (m, 2H), 6.78 (d, J=8.7 Hz, 2H), 6.64 (d, J=9.7 Hz, 1H), 6.56 (s, 1H), 6.17 (d, J=9.1 Hz, 1H), 5.88 (dd, J=9.2, 4.9 Hz, 1H), 5.09 (s, 2H), 4.97-4.94 (m, 2H), 4.80 (d, J=13.6 Hz, 1H), 3.89 (s, 3H), 3.69 (d, J=16.1 Hz, 1H), 3.63 (d, J=16.1 Hz, 1H), 3.59 (d, J=18.7 Hz, 1H), 3.53 (d, J=18.7 Hz, 1H), 2.04 (s, 3H).

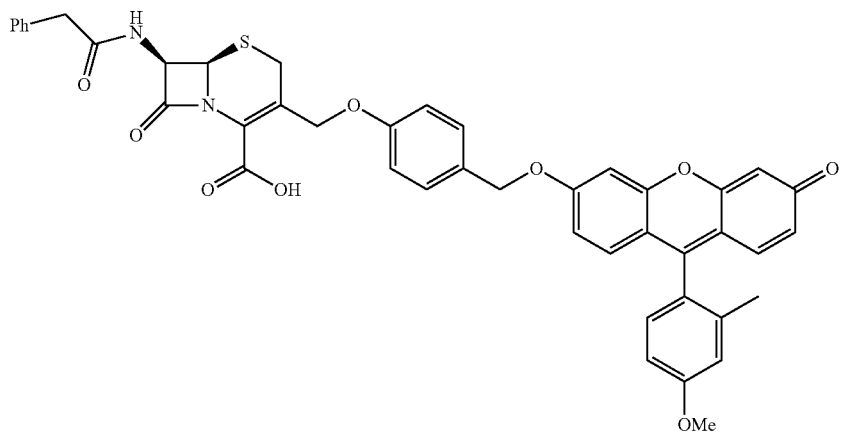

CDG-1

(6R,7R)-3-((4-(((9-(4-Methoxy-2-methylphenyl)-3-oxo-3H-xanthen-6-yl)oxy)methyl)phenoxy)methyl)-8-oxo-7-(2-phenylacetamido)-5-thia-1-azabicyclo[4.2.0]oct-2-ene-2-carboxylic acid (CDG-1)

The title compound CDG-1 was obtained from compound 11 after deprotection and RP-HPLC purification with same method as that of CDC-1. $^1$H NMR (400 MHz, DMSO) δ 9.11 (d, J=8.2 Hz, 1H), 7.49 (s, 1H), 7.43 (d, J=8.5 Hz, 2H), 7.32-6.96 (m, 13H), 6.73 (d, J=9.6 Hz, 1H), 6.63 (s, 1H), 5.67 (dd, J=8.2, 4.7 Hz, 1H), 5.27 (s, 2H), 5.09 (d, J=4.8 Hz, 1H), 4.88 (d, J=12.2 Hz, 1H), 4.83 (d, J=12.6 Hz, 1H), 3.84 (s, 3H), 3.65 (d, J=18.3 Hz, 1H), 3.58 (d, J=18.5 Hz, 1H), 3.54 (d, J=13.8 Hz, 1H), 3.47 (d, J=13.9 Hz, 1H), 1.97 (s, 3H); $^{13}$C NMR (101 MHz, DMSO) δ 180.59, 171.64, 170.66, 165.54, 164.87, 163.69, 163.42, 160.97, 160.69, 159.59, 159.52, 158.89, 138.17, 136.47, 132.40, 131.28, 131.09, 130.74, 129.68, 128.91, 127.18, 126.76, 125.15, 124.40, 118.40, 116.59, 115.97, 115.43, 112.50, 104.51, 102.06, 71.16, 67.19, 59.79, 58.20, 55.98, 42.26, 26.18, 20.21; HRMS: Calculated for $C_{44}H_{37}N_2O_9S^+$ ([M+H]$^+$): 769.2214. Found: 769.2196.

Example 4

Clinical Testing Using a Representative β-Lactamase Substrate (CDG-OMe)

In this example, clinical test results are described for Mtb using a representative β-lactamase substrate of the invention, (CDG-OMe). The results demonstrate that the Reporter Enzyme Fluorescence (REF) technology of the invention is effective for pathogen detection.

REF Diagnostic Samples.

Figure 10:
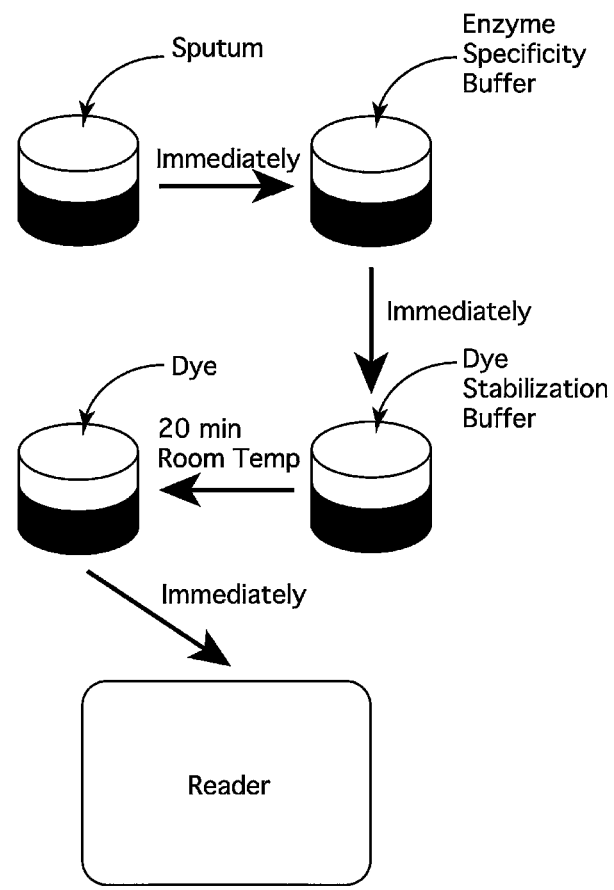
FIG. 10 illustrates a protocol for sputum processing in a representative method of the invention. In the method, all steps were carried out at room temperature. Sputum volumes can vary from 100 to 500 µL without significant impact on data obtained. Data obtained from plate reader assays. All steps completed within 30 min after obtaining sputum and with a single collection vessel without transfer steps.
Figure 11A:
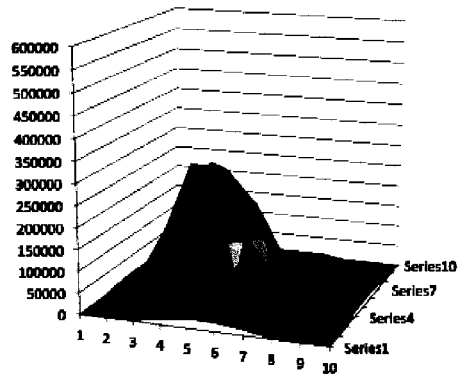
FIGS. 11A-11F are well scans obtained from smear+, culture+, REF+; smear−, culture+, REF+; and smear−, culture−, and REF− samples from Houston and Peru. Variation observed between positive and negative samples in each set is consistent with the levels of variation observed in all samples analyzed.
Figure 11B:
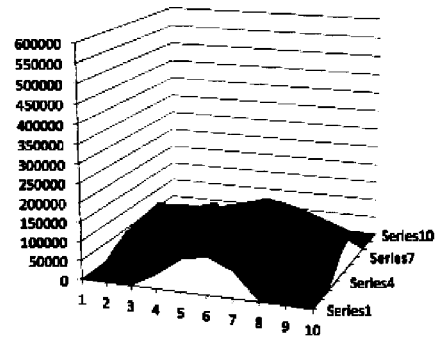
Figure 11C:
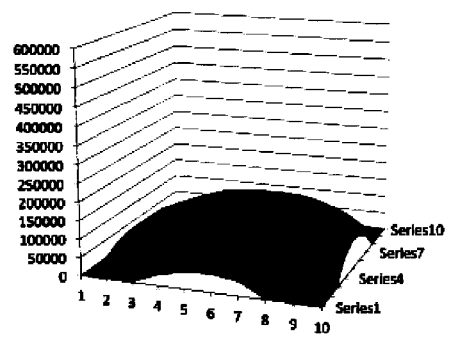
Figure 11D:
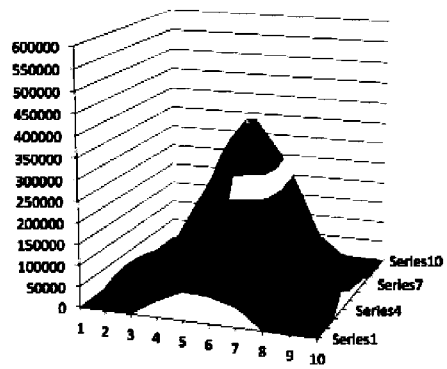
Figure 11E:
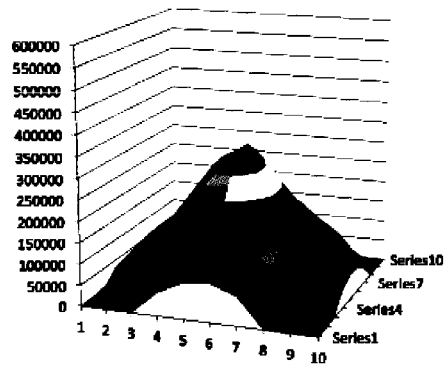
Figure 11F:
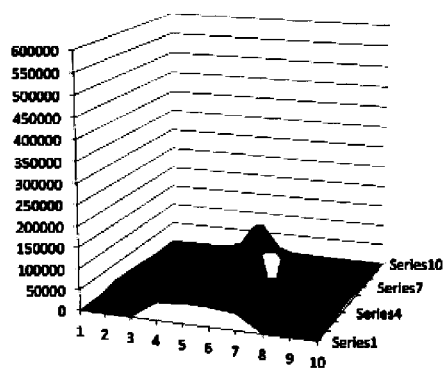

Using a preliminary, non-optimized, assay protocol (FIG. 10), 441 suspected Mtb fresh, unprocessed, diagnostic samples were obtained and evaluated REF diagnosis as compared to smear, culture and GeneXpert (Table 2).

Through the Foundation for Innovative Diagnostics (FIND), access to clinical specimens from the Lima, Peru endemic region were obtained. Access to clinical specimens from the Houston, Tex. metropolitan area were also obtained. The following describes data from Houston for 307 samples and from Peru for 134 samples. Although more than 400 samples from Houston were assayed, the first 78

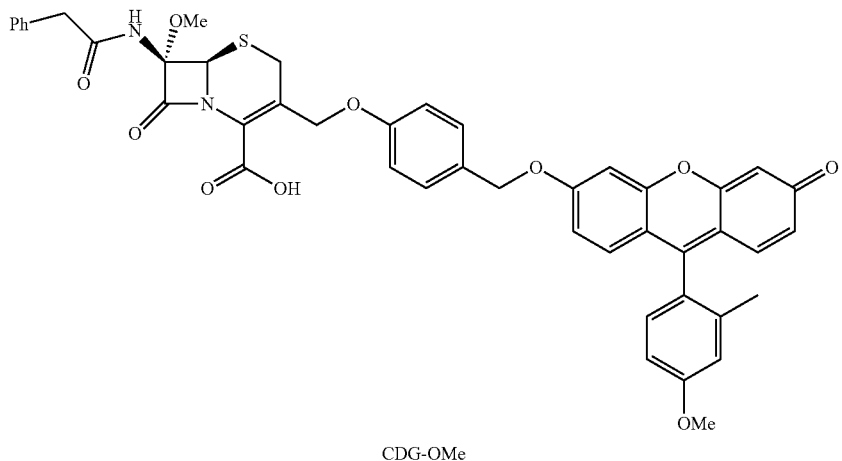 [SMILES: COc1ccc(-c2c3ccc(=O)cc-3oc3cc(OCc4ccc(OCC5=C(C(=O)O)N6C(=O)[C@](NC(=O)Cc7ccccc7)(OC)[C@H]6SC5)cc4)ccc23)c(C)c1]

CDG-OMe (6R,7S)-7-Methoxy-3-((4-(((9-(4-methoxy-2-methylphenyl)-3-oxo-3H-xanthen-6-yl)oxy)methyl)phenoxy)methyl)-8-oxo-7-(2-phenylacetamido)-5-thia-1-azabicyclo[4.2.0]oct-2-ene-2-carboxylic acid (CDG-OMe)

The title compound was prepared from compound 11 with the similar procedures used for synthesizing CDC-OMe. $^1$H NMR (400 MHz, DMSO) δ 9.44 (s, 1H), 7.45 (s, 1H), 7.42 (d, J=8.6 Hz, 2H), 7.30-7.18 (m, 6H), 7.13-7.06 (m, 4H), 7.02-6.96 (m, 3H), 6.66 (d, J=9.6 Hz, 1H), 6.54 (s, 1H), 5.25 (s, 2H), 5.15 (s, 1H), 4.82 (d, J=11.9 Hz, 1H), 4.76 (d, J=11.8 Hz, 1H), 3.84 (s, 3H), 3.40 (d, J=18.2 Hz, 1H), 3.33 (s, 3H), 1.98 (s, 3H); $^{13}$C NMR (101 MHz, DMSO) δ 181.30, 172.20, 165.48, 163.38, 161.80, 161.15, 160.90, 159.49, 158.86, 146.38, 138.15, 136.27, 132.21, 131.25, 130.90, 130.68, 129.82, 128.90, 128.73, 127.36, 127.19, 126.87, 126.77, 125.66, 124.46, 118.40, 116.56, 115.76, 115.39, 112.50, 104.66, 102.07, 95.84, 94.66, 74.90, 71.06, 67.06, 63.53, 55.97, 53.17, 42.37, 26.46, 20.19; HRMS: Calculated for $C_{45}H_{39}N_2O_{10}S^+$ ([M+H]$^+$): 799.2320. Found: 799.2302.

were used for development of the preliminary assay protocol (FIG. 10) and because culture results were not obtained, they were excluded from analysis. Samples from Houston for which culture and smear results were obtained as well as used the same REF assay protocol in all assays were selected so that the data could be analyzed as a group. In the case of the Peru samples, there were smear results and GeneXpert (MTB/RIF assay, Cepheid, Sunnyvale, Calif.) results for all 134 samples. However, because there were only culture results for 41 samples, this small set was not included in the analysis. However, no significant change in diagnostic ability in those samples were observed that was obvious. GeneXpert results were not obtained for the Houston samples because GeneXpert is not FDA approved for use in the U.S. (no clinical laboratory used the test). Most samples were processed within 7 days post-collection, with the shortest period from collection to assay being the same day for Houston and 2 days for Peru and the longest period from collection to assay being 8 days for Houston and 14 days for Peru. In the case of the Houston samples, out of the 307 included in the analysis, 9 were culture positive for *M. avium* complex (MAC) (3+), 5 culture positive for *M. fortuitum* (0+), 9 culture positive for *M. chelonae-abscessus* complex (1+), 2 culture positive for *M. gordonae* (0+), 3 culture positive for *M. mucogenicum* (1+), 1 culture positive for *M. simiae* complex (0+), 1 culture positive for *M. kansasii* (0+) and 1 culture positive for *Nocardia* sp. (1+). The number of positives by REF are shown in parentheses. All other culture positive samples were confirmed as *M. tuberculosis* by culture and HPLC. In the case of all non-*M. tuberculosis* culture positive samples, it does not appear that any of the other mycobacterial species are detected by REF, because the numbers of positives observed are likely due to the reduced specificity observed with this protocol, though in several cases, not enough samples of the species have been evaluated to be significant and allow conclusions to be drawn. These observations are consistent with another 3 *M. fortuitum* and 1 *M. avium* containing samples from those samples not included in the analysis, which were also negative by REF assay. These observations suggest that the REF diagnostic assay can differentiate *M. tuberculosis* from MAC, *M. fortuitum*, and other mycobacterial species seen in suspected tuberculosis patients, which is a great advantage since differentiating atypical mycobacteria from *M. tuberculosis* can be difficult without culture, which takes an extended period of time to obtain results. In the case of the Peru samples, all positive samples were found to be *M. tuberculosis*, making atypical mycobacteria more rarely observed in suspected Mtb samples from endemic settings as compared to such samples from the U.S. Controls were included in all assays for REF dye hydrolysis in the buffer alone, without bacteria. This control displayed similar levels of REF signal to that of negative samples in our analysis.

Use of Non-Optimized REF Diagnostic Assay Protocol to Diagnose Tuberculosis.

A summary of results using the non-optimized REF diagnostic assay with 307 Houston and 134 Peru suspected Mtb clinical specimens is shown in Table 2.

TABLE 2

Profile of suspected Mtb clinical specimens and results for REF diagnostic assay preliminary evaluation.

| Location | #Samp. | Spec. | Sens. | +PredVal. | −PredVal. |
|---|---|---|---|---|---|
| Houston | 307 | 94%* | 55% | 56% | 93% |
|  |  | 93%** | 80% | 51% | 98% |
|  |  | 91%*** | 48% | 38% | 94% |
| Peru | 134 | 78%* | 58% | 63% | 74% |
|  |  | 75%** | 58% | 57% | 76% |
|  |  | 78%*** | 58% | 63% | 74% |

All samples processed in the same protocol. Culture results are included for Houston samples and GeneXpert for Peru samples. True positives were calculated as either culture or smear positive for Houston samples and either GeneXpert or smear positive for Peru samples*, based only on smear, or based only on culture (Houston) or GeneXpert (Peru)*.
Specificity, sensitivity, positive predictive value and negative predictive value were calculated versus the true positive and true negative rate obtained in this manner.

All samples were first compared to buffer negative controls and subsequently apparent negative samples were compared to positive samples. P values were considered significant at <0.05, but in most cases P values were <0.01. P value comparisons were carried out using multiple readings on each sample as compared to multiple readings for control in buffer. All samples were evaluated in 24-well dishes with a plate reader that was configured to scan the entire well providing a similar readout for the sputum sample to that obtained with iPhone images and found to be highly sensitive. This was found to be an important component of the REF assay due to the heterogeneity of human sputum. Positive regions within the heterogeneous sputum samples were found to be most representative of the presence of Mtb and these high outliers were chosen for statistical comparison to high outliers from negative samples (FIGS. 11A-11F). Thresholds and incubation periods were chosen to provide maximal specificity and sensitivity, but variation in these parameters enabled increased sensitivity to a maximum of 100% and specificity to a maximum of 98%. Protocols that display increased sensitivity display a commensurate decrease in specificity and vice versa. The protocol was chosen to maintain a balance between maximal specificity and sensitivity, indicating that the specificity of the REF diagnostic assay is very high, from 78-94% and, despite the absence of optimization, the sensitivity is from 55-58%. Even with the current non-optimized protocol, the speed with which results can be obtained, within 30 min of obtaining the sample, absence of the need for equipment or technical proficiency and high negative predictive value of 74-93%, these observations suggest that the REF diagnostic assay would serve as a valuable diagnostic addition. These characteristics fit well within the parameters needed for a true point-of-care diagnostic method and emphasize the importance further study and optimization of the REF diagnostic assay. The promising specificity and negative predictive value, in particular, should greatly enhance clinical management of suspected tuberculosis patients through allowing more rapid follow up than is possible with other existing technologies.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound having the formula:

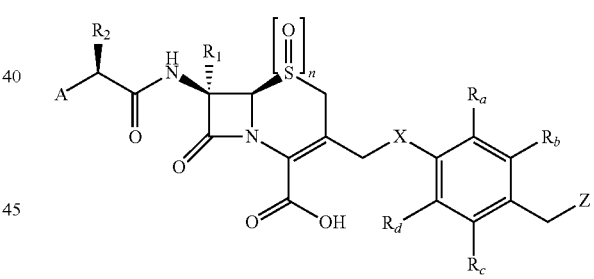

or an ester or a salt thereof,
wherein
A is selected from the group consisting of:
 (a) substituted and unsubstituted C6-C10 aryl; and
 (b) substituted and unsubstituted C3-C7 heteroaryl;
$R_1$ is selected from the group consisting of:
 (a) methoxy; and
 (b) ethoxy;
$R_2$ is selected from the group consisting of hydrogen, C1-C3 alkyl, C1-C3 alkyl substituted with one or more halogens, and substituted piperazine;
X is O or S;
$R_a$, $R_b$, $R_c$, and $R_d$ are independently selected from the group consisting of hydrogen, halogen, nitro, C1-C3 alkyl, and C1-C3 alkyl substituted with one or more halogens;

Z is a moiety that provides a fluorescent, luminescent, or colorimetric signal when released from the compound; and n is 0 or 1.

2. The compound of claim 1, wherein A is phenyl.
3. The compound of claim 1, wherein $R_1$ is methoxy.
4. The compound of claim 1, wherein X is O.
5. The compound of claim 1, wherein n is 0.
6. The compound of claim 1, wherein n is 1.
7. The compound of claim 1, wherein Z is a fluorescent moiety.
8. The compound of claim 1, wherein Z is a fluorescent phenolic dye moiety.
9. The compound of claim 1, wherein Z is selected from the group consisting of a courmarin moiety, a xanthene moiety, a resorufin moiety, a cyanine moiety, a difluoroboradiazaindacene moiety, a bimane moiety, an acridine moiety, an isoindole moiety, a dansyl moiety, an aminophthalic hydrazide moiety, an aminophthalimide moiety, an aminonaphthalimide moiety, a quinine moiety, a dicyanovinyl moiety, a tricyanovinyl moiety, an indolaniline moiety, an indamine moiety, and derivatives thereof.
10. The compound of claim 1, wherein Z is a xanthene moiety selected from the group consisting of a fluorescein moiety, a rhodol moiety, a rhodamine moiety, and derivatives thereof.
11. The compound of claim 1, wherein Z is 12. The compound of claim 1, wherein Z is wherein R' is hydrogen or aryl.

13. The compound of claim 12, wherein R' is phenyl or substituted phenyl.

14. The compound of claim 1, wherein Z is

15. A compound of claim 1 having the formula:

or an ester or a salt thereof, wherein $R_1$ is methoxy.

16. A method for detecting beta-lactamase in a sample, comprising:
   (a) contacting a sample with a compound of claim 1; and
   (b) measuring an optical signal generated from contacting the sample with the compound.

17. A method for diagnosing tuberculosis, comprising:
   (a) contacting a sample with a compound of claim 1; and
   (b) measuring an optical signal generated from contacting the sample with the compound.

18. The method of claim 17, wherein the sample is sputum, pleural fluid, spinal fluid, blood, urine, saliva, stool, tissue biopsies, tissue homogenates, directly in live animals or human patients, or a sample obtained by swabbing an area of interest on a subject.

19. The method of claim 17, wherein the sample comprises a pathogenic bacterial species selected from *Bacteroides*, *Clostridium*, *Streptococcus*, *Staphylococcus*, *Pseudomonas*, *Haemophilus*, *Legionella*, *Mycobacterium*, *Escherichia*, *Salmonella*, *Shigella*, or *Listeria*.

20. The method of claim 17, wherein measuring an optical signal comprises measuring fluorescence emission intensity.

21. The method of claim 17, wherein measuring an optical signal comprises measuring absorbance intensity.

22. The method of claim 17, wherein measuring an optical signal comprises measuring luminescence emission intensity.

* * * * *